US012725714B1

(12) United States Patent
Lombard et al.

(10) Patent No.: US 12,725,714 B1
(45) Date of Patent: Sep. 1, 2026

(54) SYSTEM AND METHOD FOR DYNAMIC ROUTE GUIDANCE DURING CONTAGION OUTBREAKS

(71) Applicant: UIPCO, LLC, San Antonio, TX (US)

(72) Inventors: John Michael Lombard, Seattle, WA (US); Lambros Petropoulos, San Antonio, TX (US)

(73) Assignee: United Services Automobile Association (USAA), San Antonio, TX (US)

( * ) Notice: Subject to any disclaimer, the term of this patent is extended or adjusted under 35 U.S.C. 154(b) by 1141 days.

(21) Appl. No.: 17/657,189

(22) Filed: Mar. 30, 2022

(51) Int. Cl.
*G16H 50/80* (2018.01)
*G05B 15/02* (2006.01)
*G07C 9/00* (2020.01)

(52) U.S. Cl.
CPC ............. *G16H 50/80* (2018.01); *G05B 15/02* (2013.01); *G07C 9/00896* (2013.01)

(58) Field of Classification Search
CPC ..... G16H 50/80; G05B 15/02; G07C 9/00896
See application file for complete search history.

(56) References Cited

U.S. PATENT DOCUMENTS

2010/0121567 A1* 5/2010 Mendelson .......... G01C 21/206 342/463
2011/0080848 A1* 4/2011 Khorashadi ............ G01C 21/20 370/254
2017/0352119 A1* 12/2017 Pittman .................. G16H 50/80
2020/0145447 A1* 5/2020 Coffey ................ H04L 63/1425
2020/0348038 A1 11/2020 Risbeck
2021/0010701 A1* 1/2021 Nesler ........................ F24F 3/14
2022/0035326 A1 2/2022 Peters
2022/0065474 A1 3/2022 Paytas
2022/0065479 A1 3/2022 Douglas
2022/0102012 A1 3/2022 Son

OTHER PUBLICATIONS

Non-Final Office Action mailed Nov. 18, 2025 for U.S. Appl. No. 17/651,996.
Non-Final Office Action mailed Apr. 18, 2025 for U.S. Appl. No. 17/651,996.
Final Office Action mailed Aug. 26, 2025 for U.S. Appl. No. 17/651,996.

* cited by examiner

*Primary Examiner* — Kidest Worku
(74) *Attorney, Agent, or Firm* — Plumsea Law Group, LLC

(57) ABSTRACT

A method and system for deploying proactive responses and personnel messaging to improve contagion-related building management are disclosed. The system and method are configured to determine whether there is a high likelihood of a contagion-related event occurring in the building, based on local device sensors. In response to the predicted contagion-related event, a controller causes a modification in building access patterns that are intended to reduce the impact of the contagion in that area. In addition, an automated personnel alert system generates customized navigational guidance to occupants to better prepare persons affected by changes in access.

20 Claims, 11 Drawing Sheets

SYSTEM AND METHOD FOR DYNAMIC ROUTE GUIDANCE DURING CONTAGION OUTBREAKS

TECHNICAL FIELD

The present disclosure generally relates to methods and systems for implementing protective responses during outbreaks of transmissible disease. More specifically, the method and system predict when an infectious agent is more likely to pose a threat to occupants, and then trigger one or more protective responses to reduce the impact of such a threat.

BACKGROUND

The advent of the COVID crisis has compelled corporations, organizations, and other large-scale entities to carefully weigh the benefits of on-site employee workforces against the risks of in-person contact in closed environments. Such decisions extend beyond COVID and the realization that large-scale contagions can occur at any time. Unprecedented challenges are forcing organizations to reconsider on how to re-introduce their on-site workforce with less risk of infection. Understanding which facilities to open, what areas of a building to make accessible, how to manage the flow of people through a facility, and rerouting personnel is a complicated problem with far reaching health, safety, and publicity consequences. There is currently no at-market tool available to help guide these decisions that is tailored for work environments and spaces that are specific to each business.

As large-scale entities evaluate whether its employees are to be permitted to return to work on-site, and how such a return should be staged, access to data accurately modeling potential outcomes of this transition is critical. For example, a company with a large campus comprising of multiple buildings, hundreds of employees, and crossovers between project teams and locations will need a mechanism by which to assess its resources and determine which facilities to open, what policies to enforce, and how many entrances and exits are necessary to avoid spreading infection while keeping track of occupant flow. The issue presents unique challenges with far reaching health and safety consequences as well as liability concerns. Furthermore, companies desire to present an image in which they are committed to making data-driven decisions that protect their workforce and community. Execution of time-sensitive protective response events in these environments is difficult, as information and action have been disconnected, making contagion management unreliable and uncoordinated.

There is a need in the art for a system and method that addresses the shortcomings discussed above.

SUMMARY

In one aspect, a method of providing dynamic navigational guidance in response to potential infectious conditions associated with a building is disclosed. The method includes a first step of receiving, by a contagion simulation model running on a computing device, a first dataset including an occupancy forecast, and a second step of producing, via the contagion simulation model and based on the first dataset, an output indicating a high likelihood of an impending hotspot event impacting a first section of a building. A third step includes determining, at the computing device, the output satisfies a required first condition for limiting access through the first door, and a fourth step includes determining, at an occupancy management system for the building, at least a first person will be impacted by limiting access through the first door. A fifth step includes identifying, at the occupancy management system, an alternative entrance that can be used by the first person to enter the building, and a sixth step includes generating first navigational guidance for the first person based on a current location of a first computing device associated with the first person. In addition, a seventh step includes causing, at the first computing device, a presentation of the first navigational guidance, the navigational guidance routing the first person from their current location to a second door corresponding to the alternative entrance.

In another aspect, a method of providing navigational guidance in response to potential infectious conditions associated with a building is also disclosed, including a first step of receiving, by a contagion simulation model running on a computing device, a first dataset including an occupancy forecast, and a second step of producing, via the contagion simulation model and based on the first dataset, an output indicating a high likelihood of an impending hotspot event impacting a first section of the building that includes a first door. The method also includes a third step of determining, at a controller module, the output satisfies a required first condition for limiting access through the first door, and a fourth step of determining, at an occupancy management system for the building, at least a first person will be impacted by limiting access through the first door. A fifth step includes identifying, at an occupancy management system for the building, an alternative entrance that can be used to enter the building, and a sixth step includes generating first navigational guidance that describes a route from the first door to the alternative entrance. Furthermore, the method includes a seventh step of limiting access through the first door during a first time period via a building automation and control system (BACS), and an eighth step of causing a presentation of the first navigational guidance at a first computing device associated with the first person prior to or during the first time period.

In another aspect, a system for providing dynamic navigational guidance in response to potential infectious conditions associated with a building includes a processor and machine-readable media including instructions which, when executed by the processor, cause the processor to receive, by a contagion simulation model running on a computing device, a first dataset including an occupancy forecast, and to produce, via the contagion simulation model and based on the first dataset, an output indicating a high likelihood of an impending hotspot event impacting a first section of a building. The instructions further cause the processor to determine, at a controller module, that the output satisfies a required first condition for limiting access through the first door. Furthermore, the instructions cause the processor to determine, at an occupancy management system for the building, at least a first person will be impacted by limiting access through the first door, and to identify, at the occupancy management system, an alternative entrance that can be used by the first person to enter the building. In addition, the instructions cause the processor to generate first navigational guidance for the first person based on a current location of a first computing device associated with the first person, and cause, at the first computing device, a presentation of the first navigational guidance, the navigational guidance routing the first person from their current location to a second door corresponding to the alternative entrance.

Other systems, methods, features, and advantages of the disclosure will be, or will become, apparent to one of ordinary skill in the art upon examination of the following figures and detailed description. It is intended that all such additional systems, methods, features, and advantages be included within this description and this summary, be within the scope of the disclosure, and be protected by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like reference numerals designate corresponding parts throughout the different views.

DETAILED DESCRIPTION

Figure 1A:
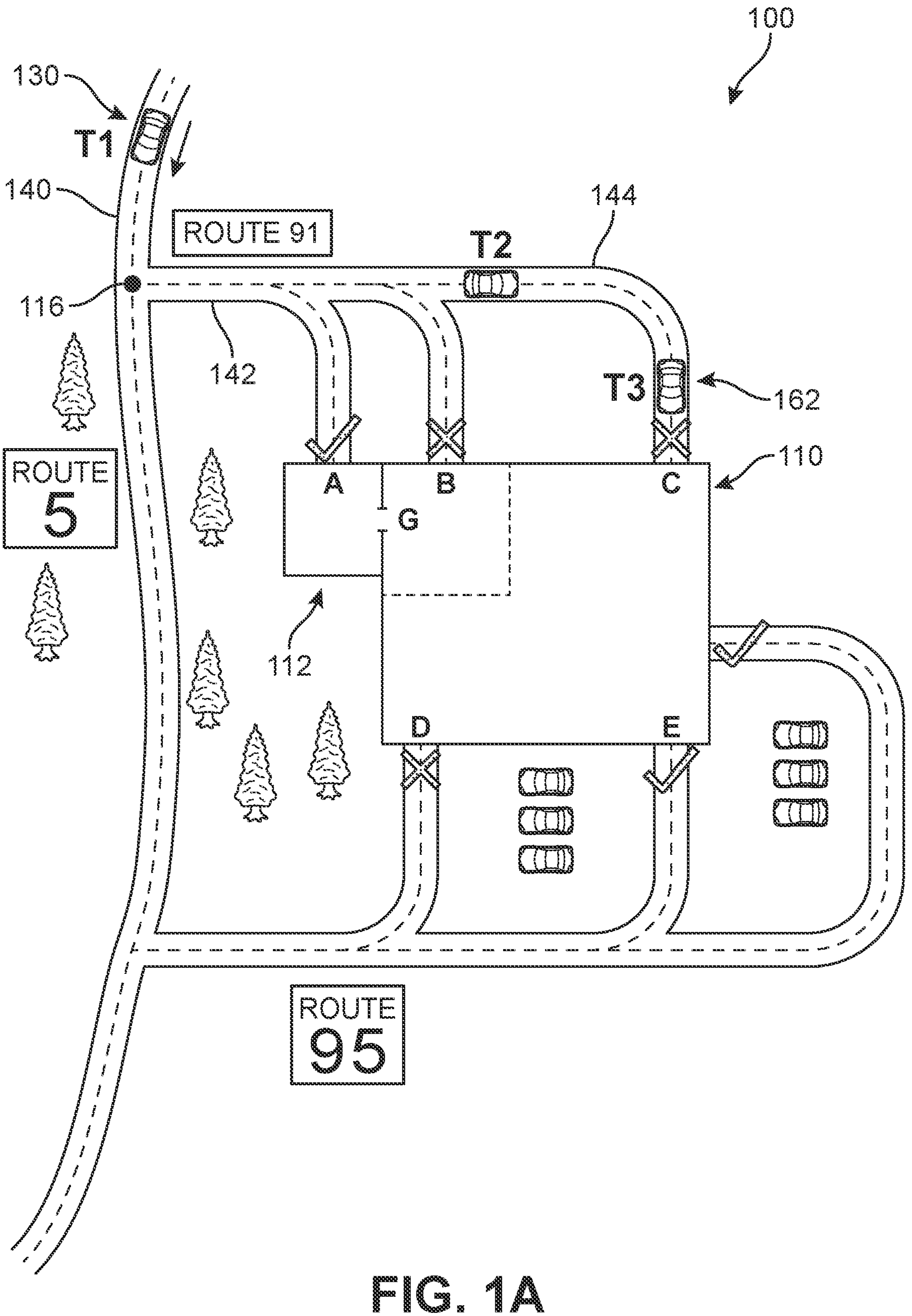
FIG. 1A depicts an overview of a scenario in which access to a door of a building is limited without notification to an approaching motorist.

Scenario testing enables decision-makers to see estimated impacts and adjust their strategies appropriately. The embodiments provide a system and method for modeling viral spread in a workplace and workforce (or other occupied structure), comprising an agent-based simulation tool for exploring the interconnected mechanisms of human behavior and viral dynamics. The output of the tool allows end-users to gain insight into the best operational approaches to ensure the safety of employees and maintain the highest level of service to consumers, and also implement an automatic protective response plan. As one example, an organization can use the tool to explore the potential impacts of contagions such as (but not limited to) COVID-19 as occupants are permitted to return to the target area or worksite. Based on the simulation, the system can be configured to generate a control signal that causes an occupancy management (computing) system (OMS) to automatically generate and convey real-time directions and instructions to personnel who are expected or otherwise likely to enter an affected building during this period.

In different embodiments, the proposed simulation tool provides the ability to explore interconnected mechanisms of human behavior and viral dynamics, based on the most recent available data from trusted health-resources. More specifically, in different embodiments, the tool may employ a model that is configured to predict and generate an approximation of (a) in-house infection rates for the target area; (b) locations of possible hotspots within the target area; and (c) how the infection rate can change with variations in occupancy and behavior. The model is based on inputs reflecting the expected movements of persons through the target area over a span of time for the specific organization, including their assigned office spaces, the layout of the offices relative to common areas such as restrooms, cafeteria, meeting rooms, elevators, etc., the probability of each person passing through a particular space and/or making contact with a common surface, as well as the social distancing restrictions that might be imposed. The output would provide a simulation of the average behavior of persons using the facilities and how the virus might spread. This type of scenario-testing software enables decision makers to see estimated impacts and adjust their strategies appropriately. The virus simulation tool can be configured as an application that may be implemented by a variety of institutions, including schools and corporate campuses.

The embodiments thereby provide a system that can facilitate a thoughtful, measured approach to contagion management in communal spaces as well as a method of use. Using this system solves the problem of timely reactive management by enabling executives and team members to see all the interdependencies between people, viral dynamics, and potential countermeasures and an automatic implementation of the designated countermeasures, or "protective actions", to be executed by on-site devices. In one embodiment, the model comprises an agent-based simulation enabling a 1:1 simulation replica of the entity's facilities, providing a low-risk approach to test, plan, and optimize management tactics for returning employees to the office or other workspace, and the countermeasures can be programmed for execution in a manner that is commensurate with the predicted degree of impact severity.

Throughout this application, references to various contagion-related terms may be used. As a general matter, the term "hotspot" is often used to refer to spatial clusters of a particular facet of a disease in infectious disease epidemiology. There are at least three hotspot types, including: (a) an area of elevated disease burden or high transmission efficiency, (b) an area with a high risk for infectious disease emergence or reemergence, and (c) an area with higher transmission efficiency or risk. In some cases, the distinction between hotspots as areas of elevated incidence or prevalence versus elevated transmission efficiency may be subtle. Whether the two measures lead one to identify the same areas as hotspots depends on the disease and how incidence and prevalence are measured. For instance, frequent malaria infection reduces the severity of infections, so an area with intermittent transmission could have more symptomatic cases than one with frequent transmission. However, if incidence is measured based on the frequency of asymptomatic parasitaemia, or symptomatic infection in young (and more likely previously uninfected) children, then high incidence areas should also correspond to areas of elevated transmission. Depending on the timescale, similarly counterintuitive results may occur when comparing the distribution of disease in endemic and epidemic contexts. For example, cholera generally transmits with higher efficiency in Bangladesh than in Zimbabwe, which experiences epidemics every 3-5 years. However, if only the overall incidence of cholera between those two countries in 2008-2009 were considered, one might be led to erroneously conclude that Zimbabwe was more of a cholera hotspot due to the large epidemic that occurred that year.

More efficient control responses may be achieved by targeting hotspots as areas of elevated transmission intensity, especially if a single area appears to sustain transmission. Various factors have been shown to create transmission hotspots, including overcrowding, poverty, lack of adequate water, sanitation, and hygiene infrastructure, etc. Features that define the hotspot will dictate the development of appropriate control measures. The implications of such heterogeneous underpinnings of transmission provide a further argument for clarity, as the misspecification of hotspots based on differential causes may result in poorly designed, misguided, and potentially costly control efforts or missed opportunities for targeting limited resources. The proposed embodiments are in particular directed toward ensuring responses to areas of elevated transmission intensity more efficient, effective, reliable, and timely.

A hotspot can also refer to an area with a high risk for infectious disease emergence or reemergence. Critical to defining emergence hotspots is the definition and identification of emergence events. An emergence event can be defined as the first reported case of a new infectious disease in a human population, or as each separate spillover event or zoonotic disease outbreak as an emergence, or the foci of reemerging diseases such as cholera, yellow fever, and typhoid, etc. Hotspots of any type do not necessarily remain stable over time, but their temporal characteristics are rarely discussed, which underlies the value of the proposed simulation-based response system. Understanding the time-scape of hotspots over time is crucial for guiding disease-control strategies. The proposed systems and method offer a mechanism by which to apply the insights obtained from the simulation in enabling effective real-world management of contagions (i.e., infectious agents), and view the potential time-scape of an event via a dashboard (see FIG. 7).

The proposed embodiments may also make reference to building automation and control systems (BACS). As a general matter, Internet of Things (IoT) devices (i.e., network-connected devices) can be placed in many physical spaces to enable people to interact with and gather information about their environment. For example, offices or homes may include numerous IoT devices that can be used to control locks, to manage indoor climate and receive climate information, to manage lighting and receive lighting information, to open and close doors, to perform cleaning functions, to control audio and/or video equipment, to provide voice interaction, to provide security and monitoring capabilities, etc. As such, IoT devices can process and generate vast amounts of information. Notably, IoT devices are not limited to use in structures such as offices or homes. For example, IoT devices may be used to track any manner of physical items (including, for example, animals such as livestock or pets), to monitor health of people or animals, and so forth.

Interconnection of computing devices has resulted in the proliferation of IoT networks, including networks of automated control systems where networks of controllers are used to control various devices. The devices are typically connected to controls and sensors. The devices can receive data from the sensors such as environmental data such as temperature, $CO_2$ concentration, airflow, or any one of a number of different environmental conditions. Based on the detected environmental conditions, the devices include computer instructions that can be executed by processors which enable the devices to use the controls to control various pieces of equipment. For example, the controls can be used to control blower motors, heaters, alarms, etc. It may be appreciated that even a small residence may include multiple different controllers and/or devices, and make use of a local BACS.

Thus, the term BACS will be used to refer to centralized systems that monitor, control, and record the functions of building services systems. Building facilities that are monitored and controlled by a reliable BACS tend to maintain the building environment more efficiently and so reduce the building's environmental impact and energy costs. The core functions of a BACS system can include one or more of the following: Maintain control of the building's environment; Operate systems according to occupancy and energy demand; Monitor and correct the performance of systems; Sound alerts as required; and other functions. Moreover, the facilities that may be controlled by a BACS system include: Mechanical systems; Plumbing; Electrical systems; Heating, ventilation and air-conditioning (HVAC); Lighting control; Security and surveillance; Alarms; Lifts; Cleaning systems; Informational systems, etc.

The proposed embodiments take advantage of a growing overlap between the functionalities of BACS and the ability to learn from accumulated sensor data to dynamically operate buildings toward the goal of greater protection of occupants from infectious agents. As will be discussed with reference to FIGS. 2 and 3, the proposed system can include one or more components such as (a) Sensors to measure values such as temperature, humidity, lighting levels, room occupancy, and so on; (b) Controllers that instigate the system's response from the collected data, using algorithms that apply logic and send commands; (c) Output devices that carry out commands from the controller; (d) communications protocol that serve as the 'language' used by the BACS components; and a (e) Dashboard (see FIG. 7) or other user interfaces for data reporting and interaction with the system.

Figure 1B:
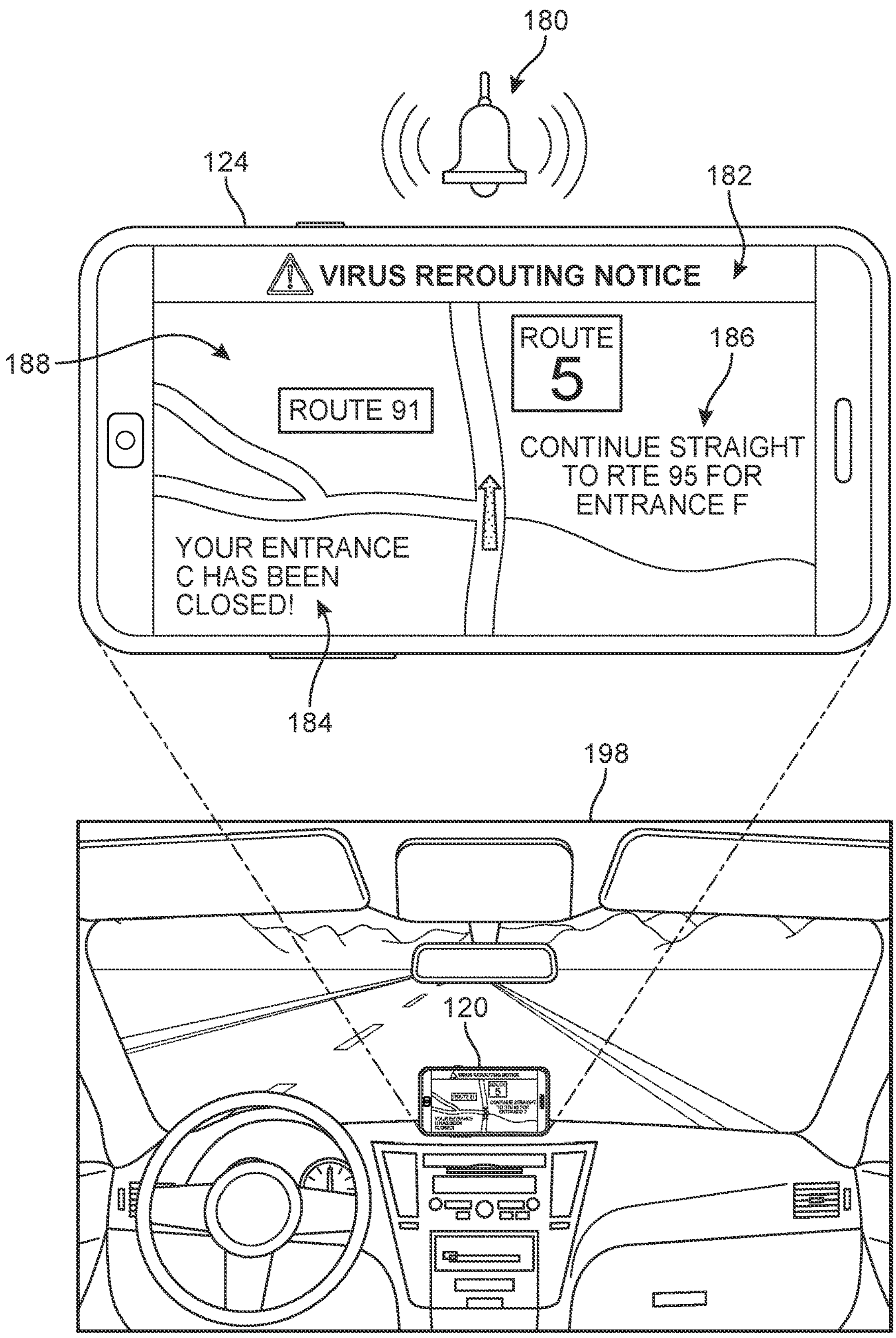
FIGS. 1B and 1C depict an overview of a scenario in which access to the door is limited and dynamic navigational guidance is provided to a motorist heading towards the building, according to an embodiment.

For purposes of introduction, an overview of one embodiment of the proposed systems and methods is illustrated with reference to FIGS. 1A-1C. In FIG. 1A, a bird's-eye view of a corporate campus 100. A vehicle 130 is shown at three points in time: T1, T2, and T3. At time T1, the vehicle 130 is traveling down a first roadway 140, as the driver heads toward work. At time T2, the vehicle 130 has turned at intersection 116 and moved onto a second roadway 144 leading to one end of a building 110 of the campus 100. At time T3, the vehicle 130 has parked in a first lot 162 adjacent to a Door "C" that leads directly to a section C of the building 110 where the driver works (Section C employee). However, unbeknownst to the driver, the campus 100 has initiated a lockdown of some of the entry points to building 110 and connected sub-building 112, including doors "B", "C", "G" and "D". Only doors "A", "E", and "F" remain open and allow access. Unfortunately, after parking in first lot 162, where the employee normally parks, the employee walks to the Door "C" and finds, to their consternation, that they cannot enter. They walk across to the next nearest entry, Door B, which is also locked. Finally, the reach Door A to enter sub-building 112, only to find the passage from sub-building 112 to building 110 via Door G has also been blocked.

Because the doors had been locked as a protective response to detection of a sudden surge in contagion (either simulated or real-time) based on new data from only hours before, it can be appreciated that the campus would have little time to post adequate signage along the roadways informing visitors and employees of these temporary changes. In this way, the employee has expended time, energy, and is now late for a meeting. Even when doors are only locked temporarily (e.g., for 20 minutes, an hour, etc.) in order to perform a cleaning or disinfection session in that area, the inconvenience and frustration caused to personnel when the attempt to enter the area and find they cannot use the expected access point can be significant.

As will be described in greater detail below, the proposed systems and methods offer a mechanism by which personnel can be alerted and rerouted before arrival at the target destination when a BACS automated (or manual) protective response disrupts or otherwise modifies the normal flow of traffic through a building or larger campus. In FIG. 1B, an example of a personnel notification app ("app") 182 running on a first mobile computing device ("first device") 120 in the vehicle 130. In this scenario, the driver receives an alert 180 via app 182 that includes a mapping interface 188 showing the driver's current location, information 184 regarding the closure of doors ("Your entrance C has been closed!") and directions 186 for rerouting ("Continue straight to Rte 95 for Entrance F"). In other words, before reaching the turn-off for their standard entrance (C), the app 182 warns the driver that entrance C is closed, and offers real-time guidance to the next nearest or convenient entrance (F).

Figure 1C:
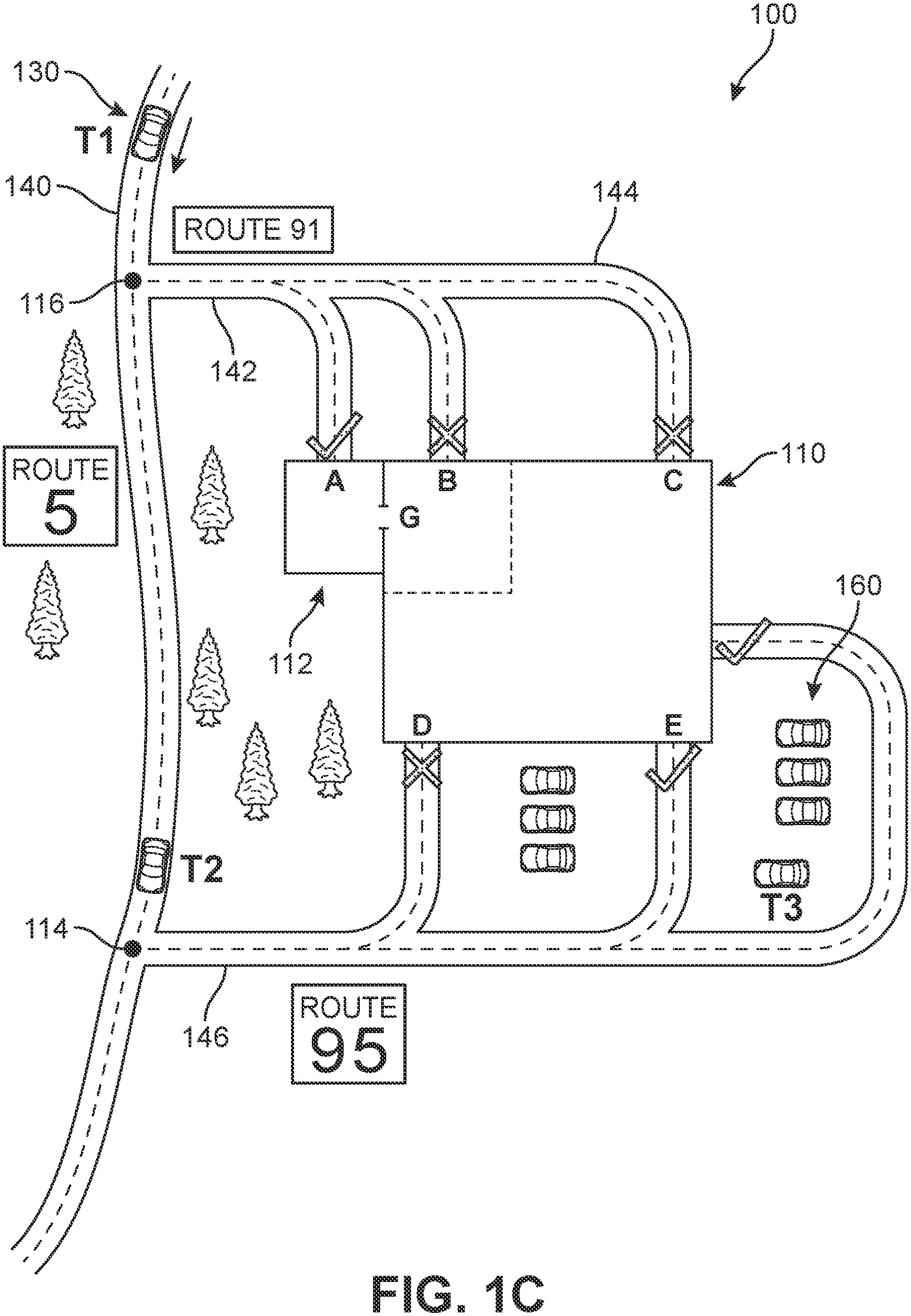

Relying on this guidance, vehicle 130 continues driving on Route 5, as shown in FIG. 1C, and avoids the wasteful scenario of FIG. 1A. In FIG. 1C, the vehicle 130 is again shown at three points in time: T1, T2, and T3. At time T1, the vehicle 130 is traveling down the first roadway 140, as the driver heads toward work. It is at or before this time that the app 182 of FIG. 1B presents the alert 180. At time T2 in FIG. 1C, the vehicle 130 has instead continued to drive along the first roadway 140 until intersection 114. Per the app's instructions, the driver turns onto a third roadway 146 until reaching Entrance F. At time T3, the vehicle 130 has parked in a second lot 160 adjacent to a Door "F" that leads to a section F of the building 110 and is directly adjacent to Section C where the driver works (Section C employee). Thus, the BACS response of locking certain doors still occurs, but with minimal frustration and expenditure of time and emotional energy for the affected employees and visitors.

It should be appreciated that while a building is referenced for implementation of the proposed systems, the term building can encompass any one of a number of different entities. For example, building may be an entire company. Alternatively or additionally, the building may be a division of a company. Alternatively or additionally, the building may be a city or town where the company has a presence. Alternatively or additionally, the building may be a single room or residence. Alternatively or additionally, the building may be a floor of a building. Alternatively or additionally, the building may be a workspace on the floor of a building, etc.

Figure 2:
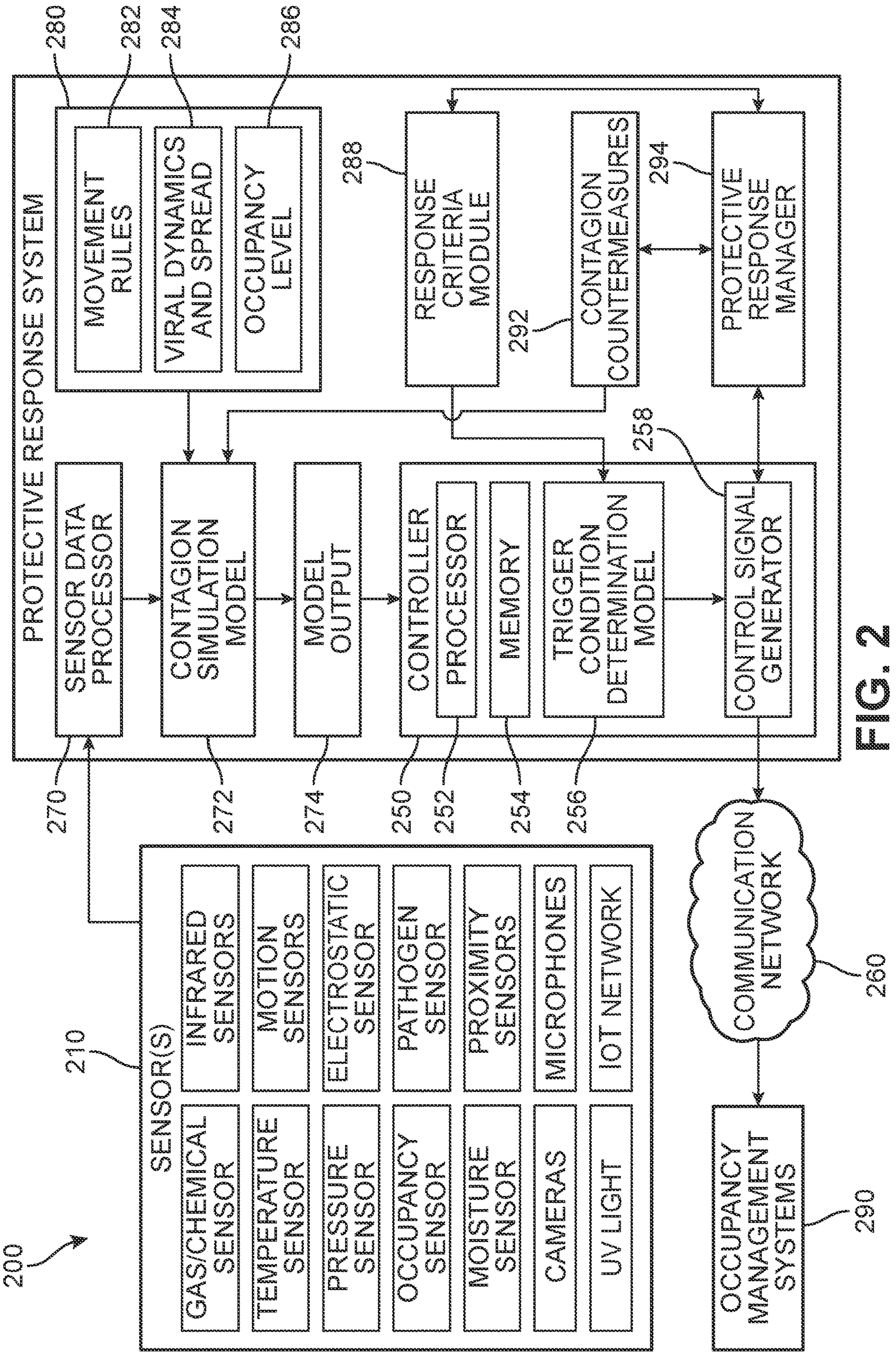
FIG. 2 is an overview of an environment for a protective response management system, according to an embodiment.
Figure 3:
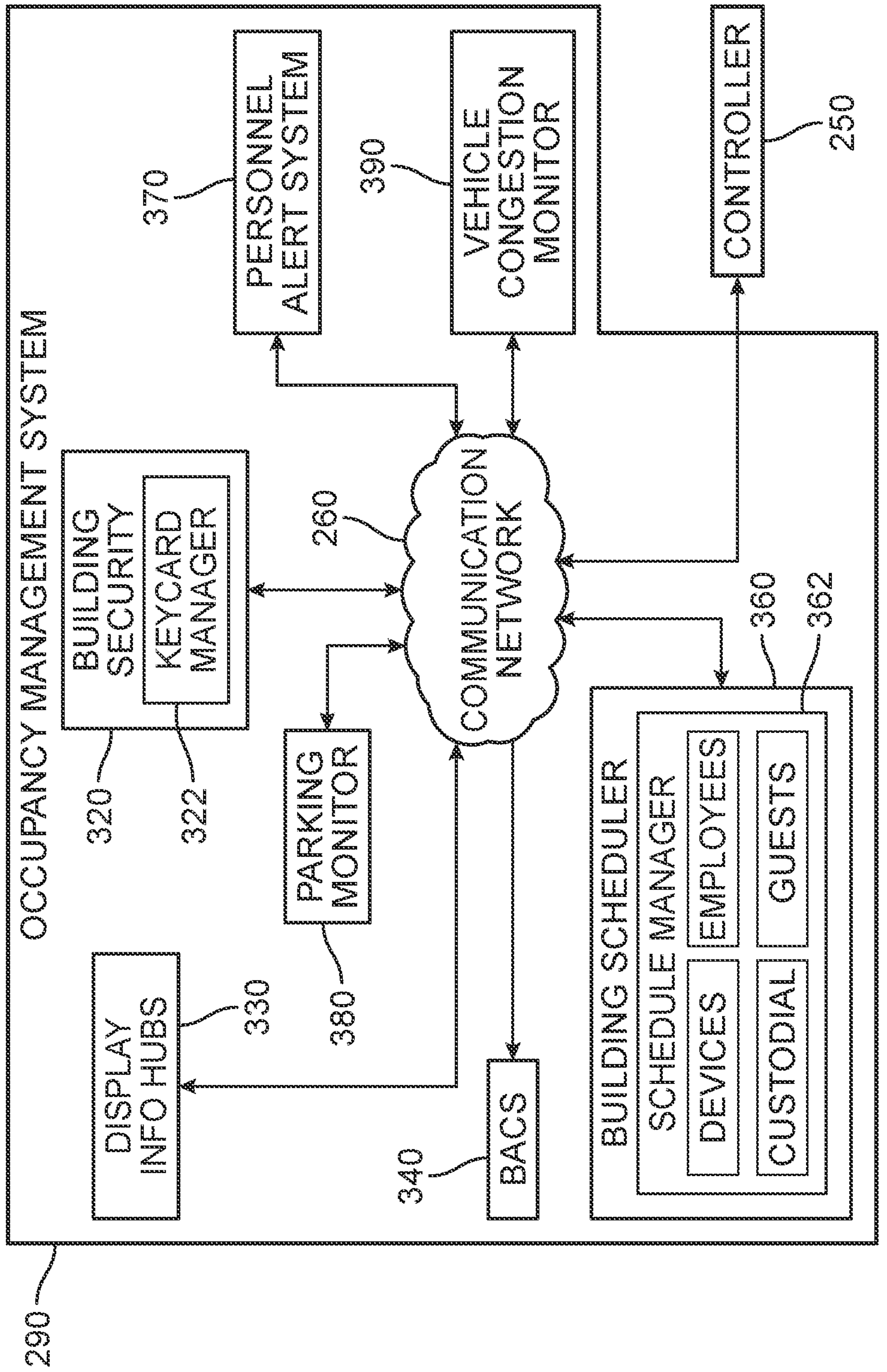
FIG. 3 is an overview of an occupancy management system, according to an embodiment.

Referring now to FIGS. 2 and 3, a protective response system 202 and its associated environment 200 incorporating and/or utilizing occupancy management system 290 is illustrated. As noted above, the proposed embodiments are configured to initiate one or more protective actions that are part of a protective response plan in response to particular output evaluations made by a contagion simulation model ("model") 254.

As a general matter, a wide range of sensor devices ("sensors") 210 can be installed in or around a building that can collect data for use by model 256. In different embodiments, the sensors 210 can include one or more types of a component, device, module, machine, or subsystem whose purpose is to detect events or changes in its environment and convey the detected information to one or more sensor data processors 252, for example for controller 250 and/or model 254. As shown in part in FIG. 2, some non-limiting examples of such sensors include (a) Smoke, Gas and Alcohol (and/or other chemicals) sensors; (b) Temperature sensors; (c) Pressure sensors; (d) Cameras and other image and/or light sensors; (e) UV light sensors; (f) Moisture/Humidity sensors; (g) Electrostatic sensors; (h) Audio sensors and other sound/volume sensors (e.g., microphones); (i) Motion/speed sensors; (I) Wind Speed sensors; (m) Proximity sensors; (n) Infrared and Heat sensors; (o) occupancy sensors; (p) pathogen sensors (e.g., devices that apply swab chemistry for effective sanitation and allergen control, pasteurization verification, and pesticide, for example using a luminometer); and/or (q) IoT network devices. In addition, in some embodiments, sensors 210 can include ultrasonic sensors, touch sensors, aerosol characterization sensors, magnetometers, color sensors, tilt sensors, and flow and level sensors. Thus, in different embodiments, sensors 210 may collect data regarding location, wind, heat/cold, congestion, temperature of occupants, proximity of occupants, surface areas, etc. around the building.

In some cases, sensors 210 can refer to one or more of a stationary internet of things (IoT) device(s) ("smart sensors") that communicate over a network. Smart sensors could comprise any of a variety of different IoT devices and other smart devices that may include one or more sensors. The smart sensors can be stationed at a wide range of locations in and around the building.

In different embodiments, data collected by sensors 210 can be conveyed to a sensor data processor 270 for managing, storing, and processing the received sensor data. The data is used to determine, in conjunction with model 272, whether the required conditions have been met for a particular trigger condition that would cause implementation of a protective response plan. Furthermore, "sensors" can be partially or entirely virtual. A sensor, as used herein, does not have to be a physical device, but rather a "sensor" output could be a value provided by another cloud service or API. For example, a "sensor" could output the current weather forecast for a building's location from NOAA.

In some embodiments, sensor data processor 270 may reside on a server computer system configured to provide access to sensor data from devices (such as IoT devices) located within physical spaces (e.g., a room within a building). The server computer system may comprise any type of computer system, including any combination of hardware and/or software that is configured to provide access to sensor data from devices located within particular physical spaces. A server computer system may include various engines, functional blocks, and components that may be implemented on a single computer system, or may be implemented as a distributed computer system that includes elements resident in a cloud environment, and/or that implement aspects of cloud computing (i.e., at least one of the various illustrated engines may be implemented locally, while at least one other engine may be implemented remotely). In addition, the various engines, functional blocks, and/or components of the server computer system may be implemented as software, hardware, or a combination of software and hardware. Although not illustrated, the various engines of the server computer system may access and/or utilize a processor and memory, such as processors and the memory, as needed, to perform their various functions.

In different embodiments, the embodiments provide for a highly accurate software model (contagion simulation model 272) that can be run on a computing system including processors and memory. Memory may comprise a non-transitory computer readable medium. Instructions stored within memory may be executed by the one or more processors. The model 272 includes at least an input module, a dependency module, and a reporting module. Reporting module may also include a visualization dashboard (see FIG. 7) that can be displayed in real-time as the model runs. In operation, input module acts to consolidate various information that may be pertinent to the simulation (simulation data 280), including movement rules 282, contagion dynamics and spread 284, expected occupancy levels and patterns 286, as well as information about modeling agents, the simulation environments, contagion countermeasures, and/or model visualization preferences. The dependency module is used to identify and form dependencies between any related aspects of a program, including modeling agents, the simulation environments, movement rules, contagion dynamics and spread, contagion countermeasures. Reporting module may be used to provide reporting dashboards as well as other information that can be used by decision-makers, executives, and team members to see the status of the simulation, including the effects of altering one or more variables, risks, issues and other aspects of a program. Moreover, visualization dashboard can be used to provide information about dependencies between various aspects of the program, as described in further detail below.

In some cases, the model 272 allows users to identify specific dependencies between two or more variables. For example, the model 272 can simulate the outcome of interactions or dependencies between a plurality of modeling agents (i.e., occupancy levels/occupancy forecast), a simulation environment, movement rules 282, viral dynamics and spread 284, contagion countermeasures 292. With these dependencies established, the tool can be used to track how one variable affects another (for example, if an increase in the number of agents causes the contagion to spread at a rate that is no longer tolerable).

In some embodiments, with respect to modeling agents, it can be understood that each agent in the model represents individual employees or personnel that would be working on-site. Agents are spatially aware, mobile, and purpose-oriented. In addition, all agents are either assumed susceptible to the contagion (e.g., COVID-19) or conditioned on a baseline percentage of natural/acquired immunity. As one example, the model will be configured such that infected agents can spread the disease by shedding the virus (e.g., coughing, sneezing, or talking) either directly to uninfected people, on surfaces that may cause indirect infections (e.g., when uninfected people touch a contaminated surface and then touch their face), and/or via air circulation systems moving air between spaces in which infected personnel are working and uninfected personnel are working.

Furthermore, in some examples, the simulation environment can represent the actual space in which the workforce (or other personnel/residents) are to return. As one example, an actual scaled floorplan of some or all portions of a building with office space, meeting space, restrooms, hallways, elevators, escalators, stairs, and cafeteria space, may be mapped. The model 272 can model the workday minute-by-minute for a specific duration such as 1 week, 30 days, 60 days, 1 year, etc. (adjustable). The model can be configured to allow agents to move freely between different spaces depending on their desires, or can impose restrictions. Based on movement rules 282, for example, and depending on the time of the day, personnel can be either at home or in the workspace. When employees are in the workspace, at each time step, they make decisions about where to go based on their needs. The model can create or identify movement targets (goals) for agents such as restrooms, cafeterias, meeting rooms, stairwells, elevators, escalators, hallways, desks, cubicles, classrooms, etc.

The model may also receive and incorporate information about potential contagion countermeasures 292. Such countermeasures can refer to mechanisms by which organizations can limit the spread of the contagion. Some examples include mask usage, social distancing, personal hygiene, facility cleaning, and vaccine uptake with conferred immunity, if it is available. The model is configured to receive values for parameters for each of these measures such as propensity, frequency, and efficacy in order to determine their effect on the spread of a disease. Other examples include occupancy restriction (e.g., limiting large restroom usage to two persons at a time) and screening at the entry/gate (e.g., actively symptomatic agents are turned away from entering the facilities with some probability). Other parameters can be included to test different scenarios as applicable.

In different embodiments, the various parameters and scenario testing data can be at least in part inputted by users of a protective response manager system 294. The protective response manager system 294 can be used to adjust or define various response thresholds and criteria 288 that will be used by a trigger condition determination module 256 when deciding whether a particular model output 274 should cause execution of a protective response plan. Each protective response plan can comprise one or more protective actions as custom selected via the protective response manager system 294, or based on default operational settings. For example, a person may interact with the protective response manager system 294 to select one or more contagion countermeasures 292 (see FIG. 4) that should be employed as part of a particular protective response plan. A set of criteria can also be established that will be used by the trigger condition determination module 256 when determining if the outcome should elicit the implementation of one of the protective response plans. In some embodiments, the protective response manager system offers a user-friendly front-end service for easy review of model outcomes and for adding or selecting contagion countermeasures that should be implemented in response to one or more defined trigger conditions.

In some cases, dependencies between two or more different variable types may be identified and created by a user. In other cases, dependencies between two or more different variable types may be automatically identified and created by an automated dependency module. Dependencies can be defined and adjusted to correspond to any number of objects associated with areas/sub-areas of physical spaces (as well as devices/sensors and individuals, including types of areas (e.g., buildings, farms, houses, apartments, conference rooms, offices, bathrooms, breakrooms, study areas, desks, chairs, and so forth), types of devices (e.g., thermostat, projector, paper towel dispenser, television, computer, and so forth), types of sensors (e.g., thermocouple, thermistor, humidity sensor, CO2 sensor, Geiger counter), and so forth. In some embodiments, an indication that a person is in a room or building or using a device or facility in the room or building from a sensor can be received. A communication interface may directly interact with the sensor (e.g., via direct signaling) or via secondary indicia (e.g., flashing lights indicative of operation). For example, the sensor may be operable to detect a signal and/or a flashing light emitted by a sanitization spraying device on a toilet that indicates a sanitization spray activation or related activity, or the spray device can directly communicate with sensor data processor 270. In various embodiments, the indication from the sensor may be related to motion detection, seat engagement, shape recognition, light (or lack of light) detection, and/or the like.

In different embodiments, an output 274 of model 272 can be received by controller 250. The output 274 can describe the contagion-related conditions that will most likely occur or be present in response to one or more countermeasures (or no countermeasure). The controller 250 may include a processor 252 and a memory 254. It should be noted that the processor 252 and the memory 254 may each represent or include multiple processors and multiple memories, respectively. The processor 252 (e.g., microprocessors) may execute software programs and/or instructions to receive an indication that a person is in a room or building or using a device or facility in the room or building from the sensors 210 and control operation of the occupancy management system 290 (see FIG. 3).

Moreover, the processor 252 may include multiple microprocessors, one or more "general-purpose" microprocessors, one or more special-purpose microprocessors, and/or one or more application specific integrated circuits (ASICS), or some combination thereof. For example, the processors 252 may include one or more reduced instruction set (RISC) processors. The memory 254 may store information such as control software, look up tables, configuration data, etc. In some embodiments, the processor 252 and/or the memory 254 may be external to the controller 250. The memory 254 may include a tangible, non-transitory, machine-readable-medium, such as a volatile memory (e.g., a random access memory (RAM)) and/or a nonvolatile memory (e.g., a read-only memory (ROM)). The memory 254 may store a variety of information and may be used for various purposes. For example, the memory 254 may store machine-readable and/or processor-executable instructions (e.g., firmware or software) for the processor 252 to execute, such as instructions for receiving an indication that a person is in a room or building or using a device or facility in the room or building from the sensors 210 and controlling operation of a specific building feature, such as a ventilation device. The memory 254 may include one or more storage devices (e.g., nonvolatile storage devices) that may include read-only memory (ROM), flash memory, a hard drive, or any other suitable optical, magnetic, or solid-state storage medium, or a combination thereof. In alternative or additional embodiments, the controller 250 may include any suitable component, such as general purpose relays, industrial relays, solid-state relays, solenoid switches, and the like.

The controller 250 may be communicatively coupled to a communication interface. The communication interface may enable the controller 250 to communicate with any suitable communication network 260. For example, the communication interface may enable the controller 250 to communicate with wireless networks (e.g., mobile, WiFi, LAN, WAN, Internet, and the like). In this manner, the communication interface may enable the controller 250 to communicate with, for example, one or more sensors 210, and/or one or more systems related to occupancy management system 290 communicatively coupled to the communication network 260. For example, the controller 250 may use the communication interface to receive model output 274.

The controller 250 may use the communication interface to control operation of the building systems. In some embodiments, the controller 250 may be part of a home automation or smart home system. For example, the controller 250 may control and/or automate lighting, heating, ventilation, air conditioning, security, home appliances (e.g., washers, dryers, ovens, refrigerators, and freezers), and the like, of a home, via a communication network (such as the communication network 260). In alternative or additional embodiments, the controller 250 may communicate with a smart home system via the communication interface.

In additional or alternative embodiments, the controller 250 may be part of or in communication with an occupancy management system (e.g., of a commercial building), as depicted in FIG. 3. For example, the controller 250 may control and/or automate lighting, heating, ventilation, air conditioning, and the like, of a building via a BACS 340 for the building. In alternative or additional embodiments, the controller 250—upon determination that a trigger condition has occurred—may communicate using control signals produced via a control signal generator 258 with the occupancy management system 290 such a personnel alert system (PAS) 370 via the communication interface over communication network 260. As noted earlier, PAS 370 can be configured to respond to signals from the controller 250 and produce customized navigational guidance.

In some embodiments, navigational guidance can be generated based on data collected from one or more building-based devices, such as building security system 320 that is configured to cause entry to be permitted or denied to specific persons, personnel types, or for access to specific doors or spaces. Typically, a keycard manager 322 can be configured to respond to such commands by disabling—for a specific period or indefinitely until the condition has been removed—a person's ability to access one or more areas of the building, or to regulate such access over a specific schedule that is coordinated along with other persons' access points and times. In response to determining a person's access to a particular entryway has been disabled, the PAS 370 will identify alternate routes to the person's final destination and present navigational guidance based on the person's preferences and settings (see FIG. 4). Furthermore, in some embodiments, controller 250 can transmit a signal to informational systems 330 that can alter presentation of information on various public display hubs in or around the building, such as at information kiosks or stations, room displays, and exterior guidance.

In yet another embodiment, controller 250 can send a signal to a building scheduler system 360 that can cause automated changes to the schedules for particular persons, for example via a schedule manager tool 362. For example, a schedule can be modified so that custodial staff are scheduled to clean one or more areas in the building following a specific model output for that area. In another example, a building schedule that had identified guests as visiting the building can be altered to cause the visit to be cancelled, rescheduled, or made virtual. In some cases, a building schedule can stagger the shifts of various employee groups based on pre-defined criteria. Finally, in some embodiments, the schedule manager 362 can be configured to disable one or more computing devices installed in the building to discourage visitors or users in a particular area. The scheduler system 360 can be the same as or connected to the building security system 320 in some embodiments. Each of these modifications to a schedule that results in changes to the building's accessibility will be noted by the PAS 370 in determining (a) whether a person is affected by the change and (b) the most efficient route for that person to now travel to their target destination that accommodates the change.

It should be understood that while the controller 250 in FIG. 2 bases its trigger event determination on output from the model, in other embodiments, the controller 250 can be configured to respond directly to sensor data that meets certain criteria. In other words, as shown in FIGS. 1A and 1B, the change in occupancy detected by the sensor array can itself be sufficient to directly cause the controller to signal the BACS to lock the door. The criteria can be selected by an end-user via the protective response manager. Thus, rather than basing a response on a potential/predicted or in the future contagion-related event, the system can be configured to respond in the moment to conditions that are in flux in real-time. The simulation model then becomes optional, for use by those who are seeking to engage in more long-term preparation.

It should be appreciated that the system is further configured to terminate the implementation of the selected protective response plan or otherwise revert to normal building operations in response to the dissipation or other change in the trigger condition. In some embodiments, normal operations can resume following a pre-specified time period in which the plan is implemented, in response to a manual selection, and/or in response to a different output from the model. Thus, doors that were locked will be automatically unlocked, keycards will be automatically re-enabled, ventilation will automatically be normalized, etc. In another example, the system can be returned to normal only after confirmation is given that the area was cleaned as scheduled by the cleaning service.

Furthermore, in some embodiments, the directions generated by the PAS 370 can be selected based at least in part on data collected by a parking monitor system 380. The parking monitor system 380 can comprise of a plurality of on-site parking lot sensors (e.g., parking spot occupancy detectors, weight sensors, image data, etc.) that will maintain a real-time record of the availability of parking spaces near each entrance. In other words, if a parking lot is nearing capacity, or is full, the PAS 370 is configured to select the next best rerouting option that would allow the person to park near the alternate entrance. This may be necessary in cases where the person has selected a preference for easy parking to accommodate the loading or unloading of contents in their vehicle, a mobility disability, weather, walkway conditions, or a desire to minimize the walk from their car to the building for any other reason.

Similarly, in some embodiments, the directions generated by the PAS 370 can be selected based at least in part on data collected by a vehicle congestion monitor system 390. The vehicle congestion monitor system 390 can comprise of on-site traffic sensors installed around the building or campus. In other words, if there is a delay for persons attempting to reach a first door, but the traffic patterns have become congested (an accident, parking lot is full, etc.) the PAS 370 is configured to select the next best rerouting option that would allow the person to drive more quickly and arrive sooner at a building entrance.

Figure 4:
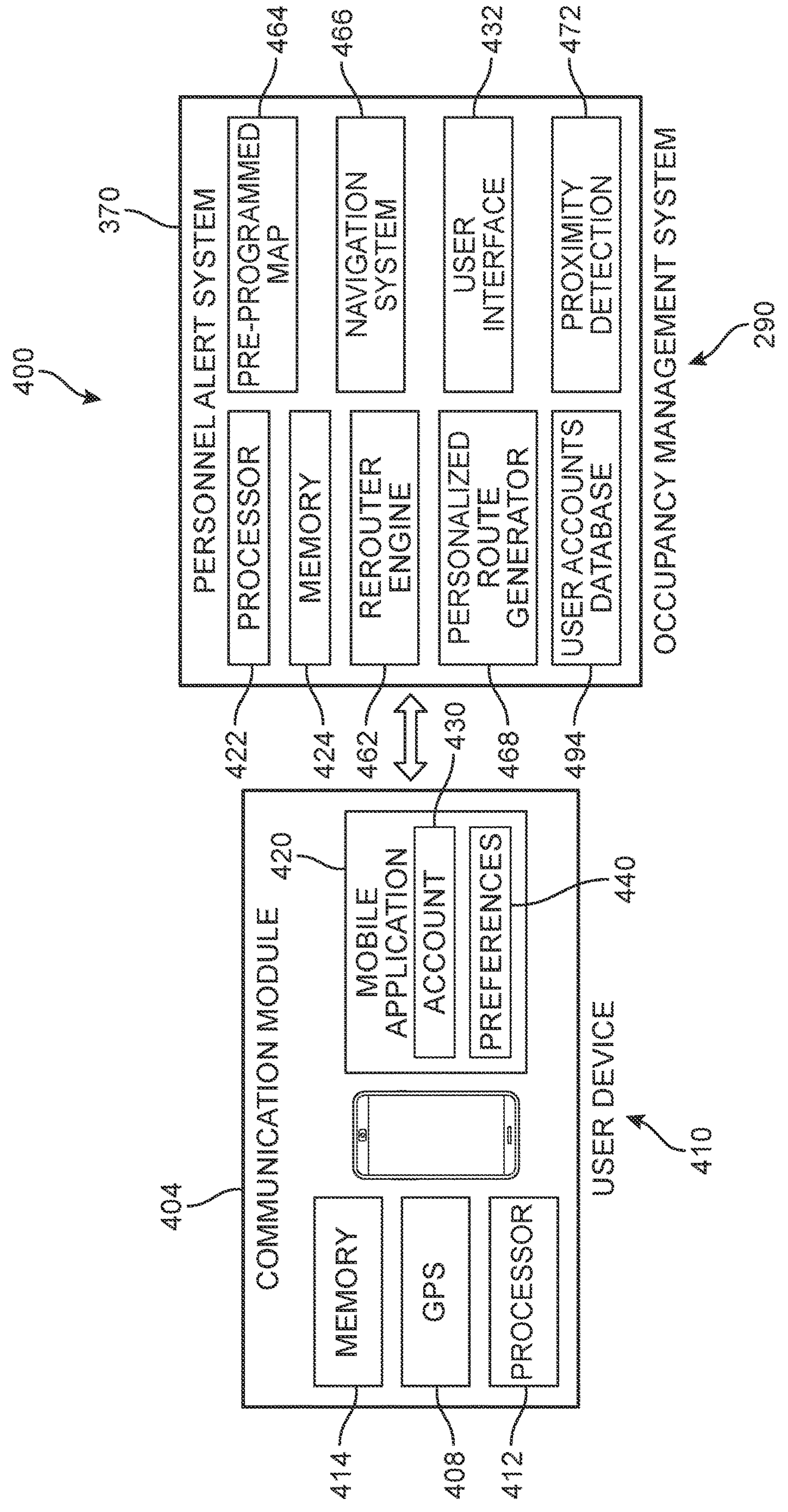
FIG. 4 is an overview of an environment for a personnel alert system, according to an embodiment.

Additional details regarding the PAS 370 are discussed now with reference to FIG. 4. In FIG. 4, a schematic diagram representing the architecture of one embodiment of a personnel guidance system 400 is illustrated. The personnel guidance system 400 includes a user device 410, such as a mobile computing device, which includes or has access to (over a network) to a mobile application ("mobile app") 420. Thus, mobile app 420 can reside entirely on the user device 410, be accessed over a network via a remote server, or include some components on user device 410 and others at the remote server. In different embodiments, such a network could include one or more Wide Area Networks (WANs), Wi-Fi networks, Bluetooth or other Personal Area Networks, cellular networks, as well as other kinds of networks.

In addition, user device 410 can include provisions for communicating with, and processing information from, a server as well as other devices (i.e., communication module 404). It may be appreciated that different devices could communicate using different networks and/or communication protocols. For purposes of this disclosure, a communication protocol refers broadly to any type of communication system that enables wireless communications to/from a mobile device. Communication module 404 of user device 410 may include a wireless connection that implements or includes components providing one or more communication protocols such as Bluetooth® radio technology, communication protocols described in IEEE 802.11 (including any IEEE 802.11 revisions) such as Wi-Fi, as well as communication protocols that rely on cellular technology (such as GSM, CDMA, UMTS, EV-DO, WiMAX, or LTE), or Zigbee® technology, among other possibilities. In many cases, the communication module is a wireless connection; however, wired connections may also be used. For example, the communication module may include a wired serial bus such as a universal serial bus or a parallel bus, among other connections. Each device may include a communication system such as a radio or other provisions for communicating using one or more communication methods. In particular, the communication system includes provisions for communicating with other nearby devices and/or a server over a network. For example, each communication system could include a Wi-Fi radio, a Bluetooth radio, and/or a cellular network radio. The user device 410 may further include one or more processors 412 and memory 414. Memory may comprise a non-transitory computer readable medium. Instructions stored within memory may be executed by the one or more processors.

In some embodiments, an end-user can interact with the proposed system, for example via the mobile app 420. In some embodiments, some or all components and features of the mobile app 420 can be downloaded to be accessible locally on the device. In other embodiments, some or all components and features can be accessed via a web-based service over a network. The mobile app 420 can offer a user settings and profile interface ("user interface") 432 for accessing and modifying settings and viewing application activity. The user interface may refer to an operating system user interface or the interface of one or more software applications that may run on the user device 410. In some embodiments, user account data can be stored in the app or at the server, and include app-related user-specific information such as user preferences 440, such as but not limited to the user's selected trigger event preferences (i.e., what type of data or situation should cause the PAS 370 to present an alert or other navigation information), the user's desired alert preferences (e.g., SMS messages, in-app messages, audio alerts, volume, visual alerts, frequency of alerts, etc.), user permissions to identify which types of input (image, sound, speed, etc.) are allowed for collection by the mobile app 420, as well as an optional app activity history repository that can store and present to the user (via user interface 432) various data reflecting past app-based alerts and responses. In some embodiments, the mobile app 420 can be configured to connect to a server (for example, via a Wi-Fi or cellular connection) to add or modify information for a user account 430, for example in a cloud-hosted user account database 494. In other embodiments, such data can be stored locally. In other embodiments, the mobile app 420 can refer to a remote service accessed by the mobile device over a network.

As noted earlier, in different embodiments, the system is configured to determine whether a person associated with or otherwise approaching the building such as an employee, contractor, guest, visitor, emergency personnel, etc. and automatically trigger one or more alerts. For example, if a change to the building operation corresponds to a triggering event with respect to the user's preferences, PAS 370 performs an automated navigation messaging operation in response to the triggering event. In some embodiments, user device 410 can include or otherwise be in communication with one or more sensor devices ("sensors") 402 that may be used to determine the user's current location. Some non-limiting examples of such sensors include, but are not limited to, image sensors (cameras), accelerometers, microphone or other audio sensors, capacitive sensors, motion sensors, heat sensors, location data, infrared (IR) sensors, time-of-flight (TOF) sensors, GPS, and/or ultrasonic sensors. In some embodiments, the mobile app 420 is configured to receive location data from a GPS 408 of user device 410 to determine the current location and heading for user.

In some embodiments, the PAS 370 will include a pre-programmed mapping module 464 that includes information about the building, including routes within the building from one section to another, accessibility options (stairwells, ramps, elevators, escalators, trams, etc.), locations of exits, and other such building features. These building features can be inputted by the system manager (manually), and/or be automatically harvested from building diagrams and architectural plans. In some embodiments, the PAS 370 will receive data specifically identifying in order of ease-of-use, which entrances are best for a particular building area, and for a particular type of person (employee, contractor, guest, maintenance, disabled, delivery, etc.). In addition, PAS 370 includes an intelligent navigation system 466 that is configured to identify path(s) that can connect two or more points based on information stored in the pre-programmed mapping module 464. A rerouter engine 462 will refer to this collection of paths when determining how to guide a person from a first point who wished to enter via a second point that is now closed. The rerouter engine 462 takes into account the building map data, the navigation data, the user's desired destination into or out of the building, user preferences, weather (in cases of outdoor travel), any building policies, and other data as collected by various devices of the occupancy management system 290 (see FIG. 3), and determine a listing of which routes are acceptable in order of distance and/or average/expected travel time. Finally, personalized route generator 468, referring to the user's current location, will generate instructions for the user to guide them around the blocked area to their desired target destination using the first route identified by the rerouter engineer 462. If a user indicates manually that this route is unacceptable or undesirable for any reason, the next route on the listing may be presented (and so forth).

It should be understood that in other implementations, environment 200 in FIG. 2 and personnel guidance system 400 of FIG. 4 can include additional or fewer modules or can include one or more additional computing devices or related server devices. The modules can be associated with the various local computing devices and, for example, can be disposed within the computing device. In alternative implementations, the modules can include independent computing devices that are coupled to, and in data communication with, the local computing devices. As used in this description, the term "module" is intended to include, but is not limited to, one or more computers, processing units, or devices configured to execute one or more software programs that include program code that causes a processing device(s) or unit(s) of the computer to execute one or more functions. Processing units can include one or more processors (e.g., microprocessors or central processing units (CPUs)), graphics processing units (GPUs), application specific integrated circuits (ASICs), or a combination of different processors.

In alternative embodiments, systems and modules can each include other computing resources/devices (e.g., cloud-based servers) that provide additional processing options for performing one or more of the machine learning determinations and calculations. The processing units or devices can further include one or more memory units or memory banks. In some implementations, the processing units execute programmed instructions stored in memory to cause system, devices, and modules to perform one or more functions described herein. The memory units/banks can include one or more non-transitory machine-readable storage mediums. The non-transitory machine-readable storage medium can include solid-state memory, magnetic disk, and optical disk, a random-access memory (RAM), a read-only memory (ROM), an erasable programmable read-only memory (e.g., EPROM, EEPROM, or Flash memory), or any other tangible medium capable of storing information.

Figure 5A:
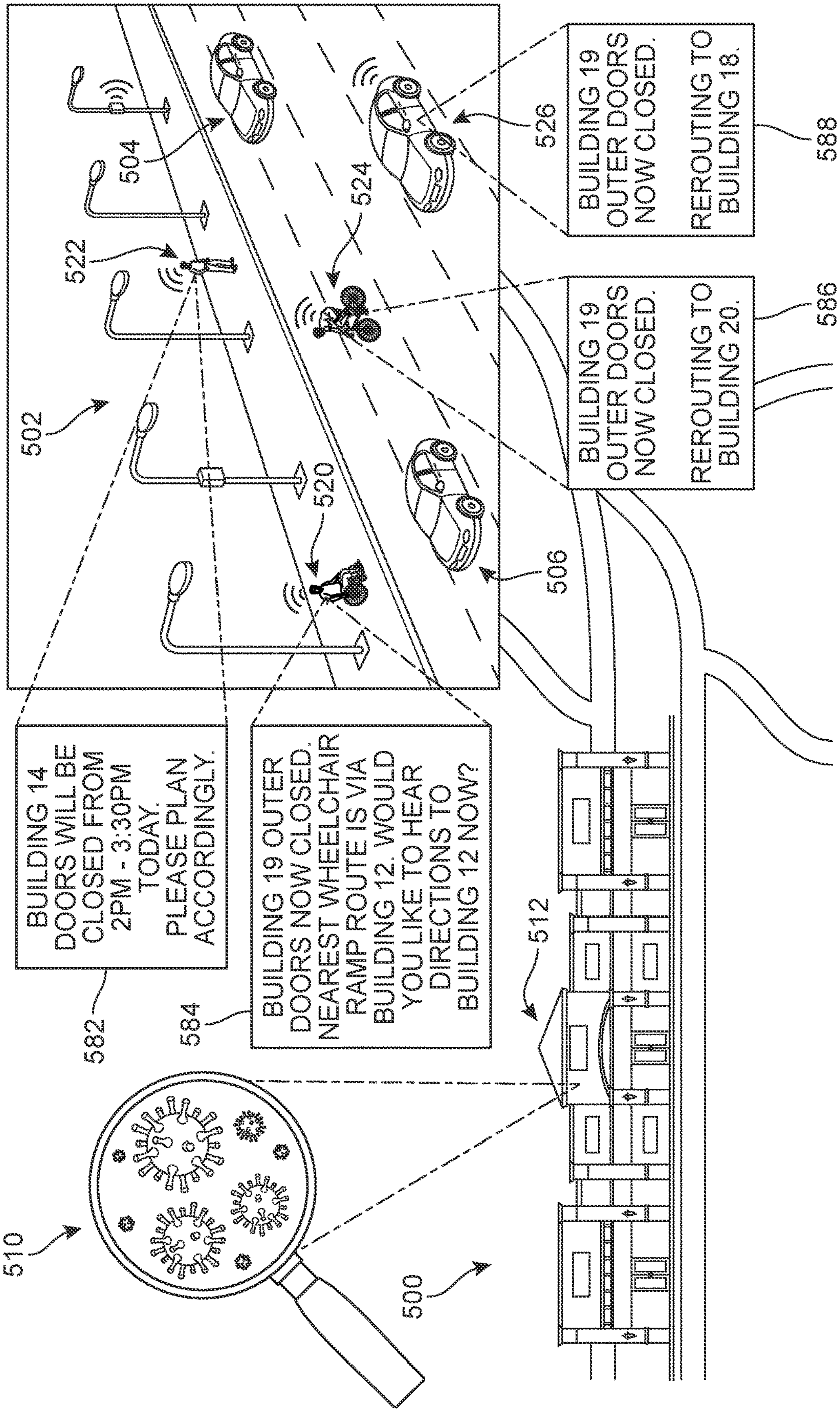
FIGS. 5A and 5B are an example of the system causing presentation of tailored navigational guidance messages to personnel approaching a building, according to an embodiment.
Figure 5B:
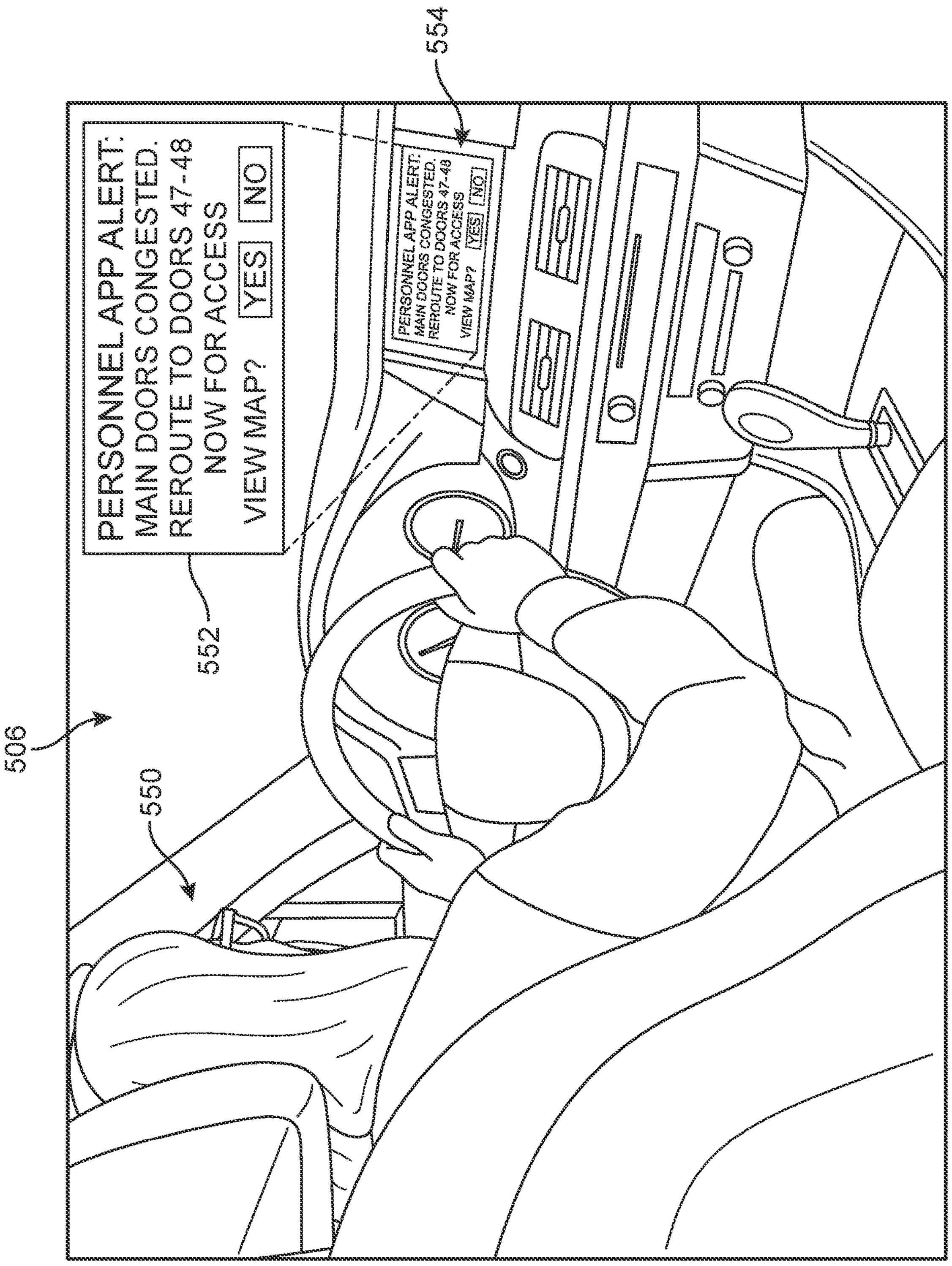
Figure 6:
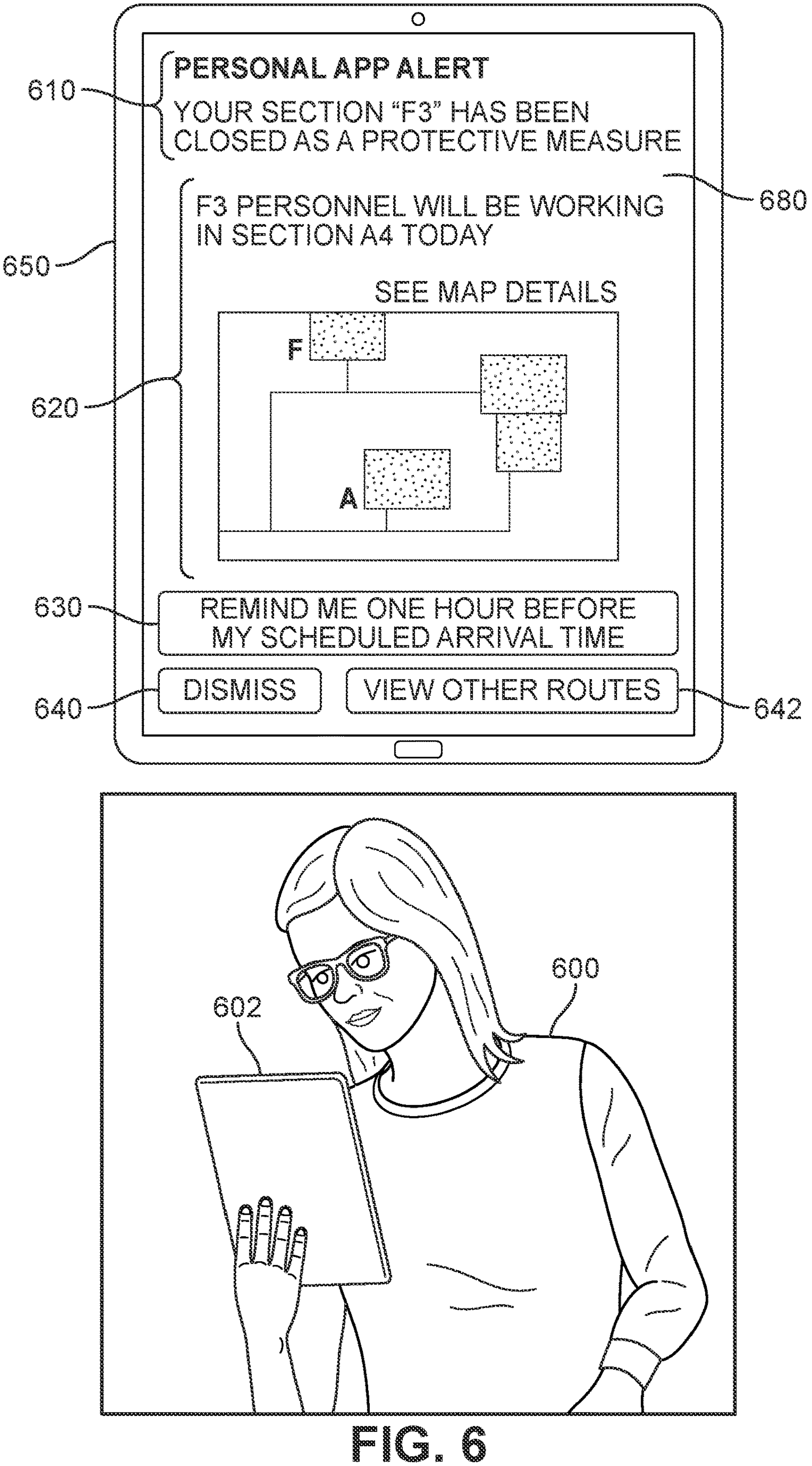
FIG. 6 is an example of the system causing presentation of a message to a person likely to be impacted by the change in access to the building, according to an embodiment.

For purposes of clarity, examples of some of the proposed systems and methods are shown in FIGS. 5A, 5B, and 6. In FIG. 5A, based on a simulation output 510 for a first area 512 of a building campus ("campus") 500, a controller may determine that the first area 512 has a high likelihood of becoming (or has become) a hotspot zone. This can be based on sensor data collected by on-site sensors. In other words, for purposes of this example, the controller determines that a trigger condition has occurred, and a signal is transmitted to a building system that will initiate execution of one or more protective actions such as a partial building closure. For example, the system can cause the first area 512 to be closed off by a locking mechanism or change to keycard access. In another example, the system can cause the schedule for custodial services to be modified in order to initiate a cleansing session to occur at first area 512 as soon as possible, rather than at the regularly scheduled time, such that cleaning personnel may be permitted entry to first area 512 while other persons will be blocked.

Once there is a building area closure that can affect the flow of persons in and out (or through) the campus 500, the occupancy management system will assess and determine who the affected personnel are. The affected personnel can include all personnel associated with the campus 500, or only (a) those persons who are scheduled to enter or use the campus 500 during a certain timespan, (b) those persons who are identified as working in or near the first area 512, and (c) those persons who are likely to pass through or visit the first area 512. In some embodiments, the occupancy management system will also refer to building scheduler (see FIG. 3) to identify whether any guests were scheduled to visit first area 512, and send these guests a personalized message via text, email, automated phone call (i.e., without requiring them to have access to the app) that avoids the closed doors, and redirects them to their target destination. Thus, in different embodiments, the app may not be required when providing static guidance or instructions, but can be required to provide dynamic (real-time) navigation.

Once the system identifies the persons who may potentially be impacted by the changes in building access, navigational guidance tailored to the person's destination and preferences will be generated. For purposes of illustration, some examples of navigational guidance are depicted in FIG. 5A for persons traveling on or positioned near campus road 700 leading to campus 500. In a first example, as soon as the system determines that doors for Building 14 should be closed for cleaning later that afternoon, a pedestrian 522 receives (via text, call, email, or an app on their mobile device) a first tailored message 582 "Building 14 doors will be closed from 2 μm to 3:30 pm today. Please plan accordingly" that is based on data that the pedestrian 522 will be visiting the campus 500 today, that it is not yet 2 μm and so they may still have access via Building 14, that the person is walking (and will not require use of a nearby parking lot), and there is a high likelihood that they plan to use Building 14 or nearby areas today.

In a second example, as soon as system determines the outer doors for Building 19 are locked, a handicapped person 520 receives (via text, call, email, or an app on their mobile device) a second tailored message 584 "Building 19 outer doors are now closed. Nearest wheelchair ramp route is via Building 12. Would you like to hear directions to Building 12 now?" that is based on data that the person 520 will be visiting the campus 500 today, that they have identified as having a condition requiring ADA access, and there is a high likelihood that they plan to use Building 19 or nearby areas today. In a third example, as system determines the outer doors for Building 19 are locked, a cyclist 524 receives (via text, call, email, or an app on their mobile device) a third tailored message 586 "Building 19 outer doors are now closed. Rerouting to Building 20" that is based on data that the cyclist 524 will be visiting the campus 500 today, and there is a high likelihood that they plan to use Building 19 or nearby areas today. In an alternative embodiment, had cyclist 524 included a preference that they always be routed to an entrance that has bike storage capacity, the message would be modified to identify the next nearest building that also includes bike storage.

In a fourth example, as system determines the outer doors for Building 19 are locked, a motorist 526 receives (via text, call, email, or an app on their mobile device) a fourth tailored message 588 "Building 19 outer doors are now closed. Rerouting to Building 18" that is based on data that the motorist 526 will be visiting the campus 500 today, there is a high likelihood that they plan to use Building 19 or nearby areas today, and that the parking for Building 20 (the next closest entrance) is full but the parking near Building 18 still has space. In an alternative embodiment, had motorist 526 included a preference that they always be routed to an entrance regardless of parking capacity, the message would be modified to identify the nearest building (e.g., Building 20) instead. A remaining vehicle 504, not being registered with the system and/or not being identified as being impacted by the closure, does not receive a message.

An alternate, fifth example is shown in FIG. 5B, where an interior of a car 506 depicted in FIG. 5A is shown. A driver 550 receives a message via her car's onboard computing system 554, which is registered with the PAS and is currently running the PAS app. When PAS detects that the driver 550 is approaching the campus, it can assess the current status of the buildings on the campus. In other words, in response to sensor data indicating that the driver is heading towards the campus, the system can review whether there are any closures that might impact her. In this case, the PAS generates a message 552 "Personnel App Alert: Main Doors congested. Reroute to Doors 47-48 now for access. View Map?YES/NO". The message 552 is a more general message that is presented for persons who are known to be approaching the campus, and warns them of the need to reroute. In this case, the doors are not closed, but are congested to the extent that the simulation determines is unsafe with respect to contagion transmission. In response, PAS requests that personnel no longer use the main entrance, but instead detour to a different set of doors that will reduce the likelihood of transmission. In some embodiments, the message 552 can also include selectable options for generating a map and real-time navigation to guide the driver 550 from their current location (per the GPS for onboard computing device) to the recommended secondary doors (Doors 47-48).

In different embodiments, the system includes provisions for generating customized real-time alerts and information for persons regardless of their proximity to the building to allow personnel to be prepared for on-site changes that could affect their workday. For example, FIG. 6 presents an embodiment of a mobile app 630 running on a tablet computing device 602. An employee 600 has just received a notification 610 ("Personnel App Alert/Your section 'F3' has been closed as a protective measure. F3 personnel will be working in section A4 today"). The notification 610 was transmitted only to those employees whose schedules (as stored in the occupancy management system) indicate that they will be working today and are associated with the affected sections (e.g., F3, A4). In some embodiments, a map 620 can also be generated and presented, showing the route between the initial destination (F3) and the new destination (A4). In one embodiment, the mobile app 630 can include a reminder option 630 configured to 'snooze' or otherwise cause presentation of additional reminders, or to close the notification (dismiss option 640). In another embodiment, the user can select a navigation option 642 to request the presentation of alternate routes to the new destination by the PAS.

Figure 7:
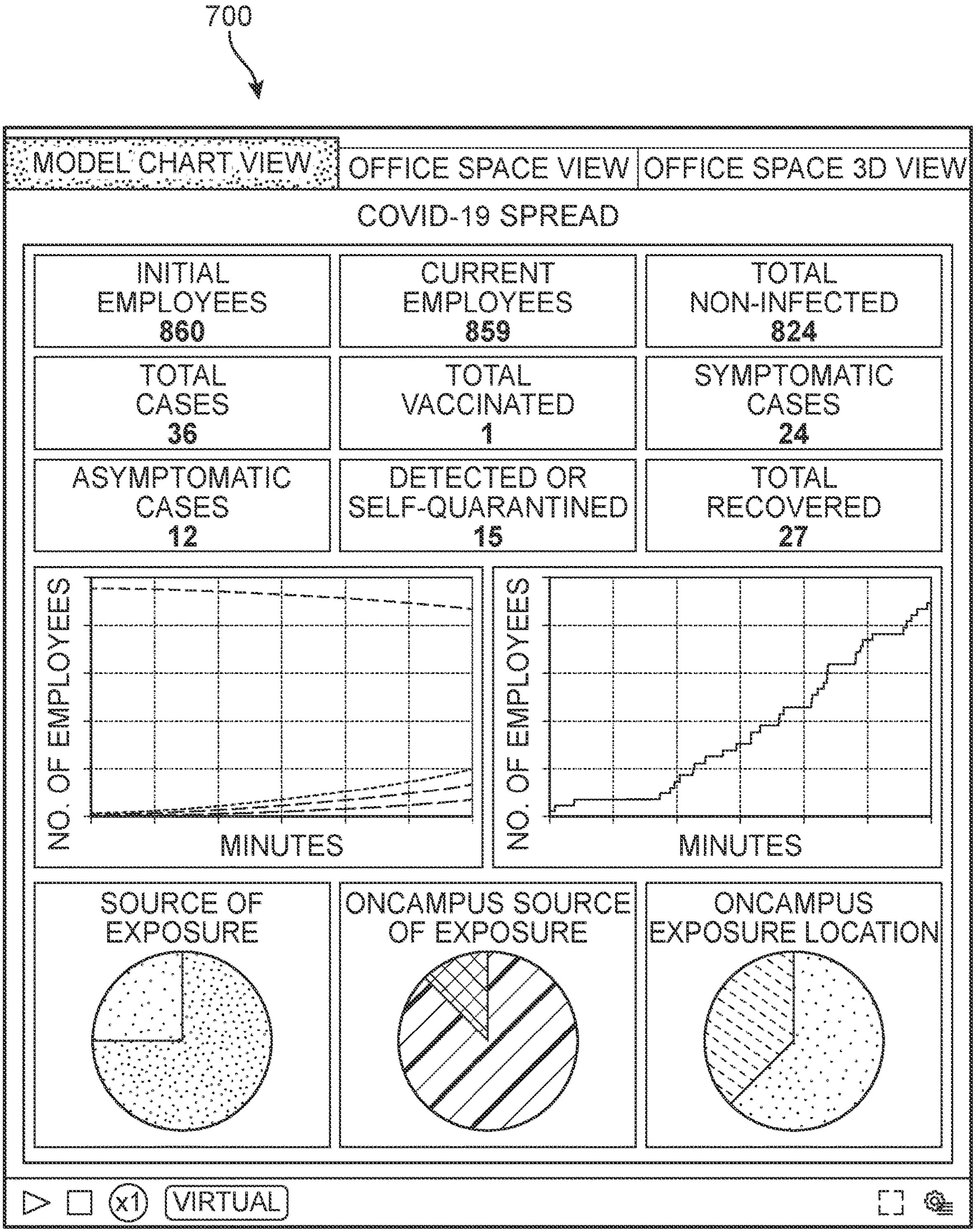
FIG. 7 depicts an example of a visualization dashboard for an end-user to interact with aspects of the simulation model, according to an embodiment.

As noted above, embodiments of the proposed systems can include mechanisms by which end-users may interact with elements of the program, input or modify various operational settings and parameters, adjust trigger criteria and response plan actions, add or change the countermeasures available, and/or view simulation outputs. In FIG. 7 a non-limiting example of a user interface ("interface") 700 is depicted. Such an interface can be presented on a display of a computing device, offering content via native controls included in the interface. Throughout this application, an "interface" may be understood to refer to a mechanism for communicating content through a client application to an application user. In some examples, interfaces may include pop-up windows that may be presented to a user via native application user interfaces (UIs), controls, actuatable interfaces, interactive buttons or other objects that may be shown to a user through native application UIs, as well as mechanisms that are native to a particular application for presenting associated content with those native controls. In addition, the terms "actuation" or "actuation event" refers to an event (or specific sequence of events) associated with a particular input or use of an application via an interface, which can trigger a change in the display of the application. This can include selections or other user interactions with the application, such as a selection of an option offered via a native control, or a 'click', toggle, voice command, or other input actions (such as a mouse left-button or right-button click, a touchscreen tap, a selection of data, or other input types). Furthermore, a "native control" refers to a mechanism for communicating content through a client application to an application user. For example, native controls may include actuatable or selectable options or “buttons” that may be presented to a user via native application UIs, touch-screen access points, menus items, or other objects that may be shown to a user through native application UIs, segments of a larger interface, as well as mechanisms that are native to a particular application for presenting associated content with those native controls. The term “asset” refers to content that may be presented in association with a native control in a native application. As some non-limiting examples, an asset may include text in an actuatable pop-up window, audio associated with the interactive click of a button or other native application object, video associated with a teaching user interface, or other such information presentation.

In some embodiments (not shown in the drawings), the interface can include a welcome or header message(s), and/or a plurality of data input fields can also be presented. Some non-limiting examples of such fields can include options directed to identification of the account owner and other users (e.g., name, phone number, address). In addition, the interface can provide a plurality of selectable options, such as navigation options (e.g., “Back”, “Save”, “Next”), or additional menu options for accessing other features or aspects of the profile. As a general matter, it should be understood that the text and specific wording shown in the figures are for purposes of illustration only and in no way limit the manner by which the application may communicate or receive information. In addition, in other embodiments, one or more options or other fields and text may appear differently and/or may be displayed or generated anywhere else on the screen(s) associated with the user’s system, including spaced apart from, adjacent to, or around the user interface. In other words, the figures present only one possible layout of the interface, and do not in any way limit the presentation arrangement of any of the disclosed features.

A variety of different program-related dashboard content can be made available via the user interface 700. The reports and/or dashboards may include charts showing information related to one or more simulation parameters or predictions. As one example, a dashboard could include charts that show relationships related to virus spread. As another example, a dashboard could include charts that show overall employee health, including information about the number of employees in a specific part of a building that have become contagious.

For purposes of the example in FIG. 7, the contagion simulation model may have been configured with the following parameters: Occupancy Restriction at strict enforcement; Restroom—2 Person limit; Café (Market Place)—2 Person limit; Elevator—2 Person limit; Restrooms Availability—50%; Entire office sanitization—2 times per day; Efficacy of Fever Detection at the door—80%, and other such parameters. In other words, the simulation need not only produce outcomes based on zero countermeasures; instead, the simulation can accommodate the effect of a wide variety of countermeasures and output an expected or most likely outcome based on the selected countermeasures.

For purposes of illustration, the simulation example in FIG. 7 reflects a hypothetical baseline of 860 employees that could be working in a multi-floor multi-building office environment under strict return-to-work (RTW) countermeasures and the contagion COVID19 condition. The example comprises a first sequence of run-time model interfaces and informative graphics that can be generated to represent the model changing over time. In addition, in some embodiments, a map view depicting the movement of agents throughout the simulation space over time may be generated. In other embodiments, multiple outputs can be generated based on the varying parameters to illustrate the power of the model in different contexts. A comparison can then be made—such as between a scenario of returning to the office under strict countermeasures and a scenario of returning to the office without enforcing the usage of face coverings inside the facilities.

For each scenario, examples of possible contour plots can be produced to represent the informative capabilities. One example can capture predicted internal infection rates under variation of both occupancy levels and external viral prevalence in the local community. Another example can indicate a metric of relative risk of infection, comparing the proportion of infections occurring inside facilities to those outside from the same population during the same time interval. In some examples, heat maps indicating locations of likely infections in the digitized floorplans can be generated—even for multiple scenarios, such as at: ~10% and 50% occupancy rates with all mitigation techniques active. The contour plots provide decision makers the ability to set risk thresholds via the protective response manager in anticipation of expected consequences to their operational plans. The heatmaps allow for facility engineers to proactively target hot-spots with additional cleaning or social-distancing enforcement. The comparison between the scenarios with and without face coverings indicate the importance of this life-saving countermeasure, without which the organization will quickly become overwhelmed with infections.

Thus, it can be appreciated that the dynamic modeling allows the end-user to easily understand the effects of various countermeasures, occupancy levels, and other variable changes can have on the infection rate. With the strict countermeasures in place, an internal infection rate estimated by the simulation may be under 1% at the end of 60 days. However, as the occupancy is increased beyond 30% capacity, the simulation outputs an assessment that the infection likelihood becomes equally risky inside and outside the facility, indicating a tipping point where the mitigation techniques are insufficient against the density of individuals. Similarly, the simulation could determine that relaxing face-coverings would cause a spike to nearly 90% internal infections within 60 days at maximum occupancy and worst-case simulated environmental viral prevalence. It should be understood that the simulation results described herein are hypothetical and provided for informational purposes only in order to illustrate the tool’s planning and strategic response capabilities. The model is configured to be re-calibrated for applications in real-world scenarios.

As described herein, a tool implementing an agent-based simulation model for exploring the interconnected mechanisms of human behavior and viral dynamics to gain insight into the best operational approaches to ensure the safety of employees is provided. Conventional simulation models do not incorporate the dynamics of the virus within the host as well as the agent’s daily activities and movements in a single model framework. The proposed tool explicitly represents the dynamics of viral transmission from person-to-person, surface-to-person, air-to-person, viral replication and interaction within-host, agent daily activity and movement in spatial space, and different counter measures that affect the spread of the infection. The tool enables decision-makers to explore estimated impacts of viruses such as COVID-19 as well as other contagions and adjust their strategies appropriately.

Figure 8:
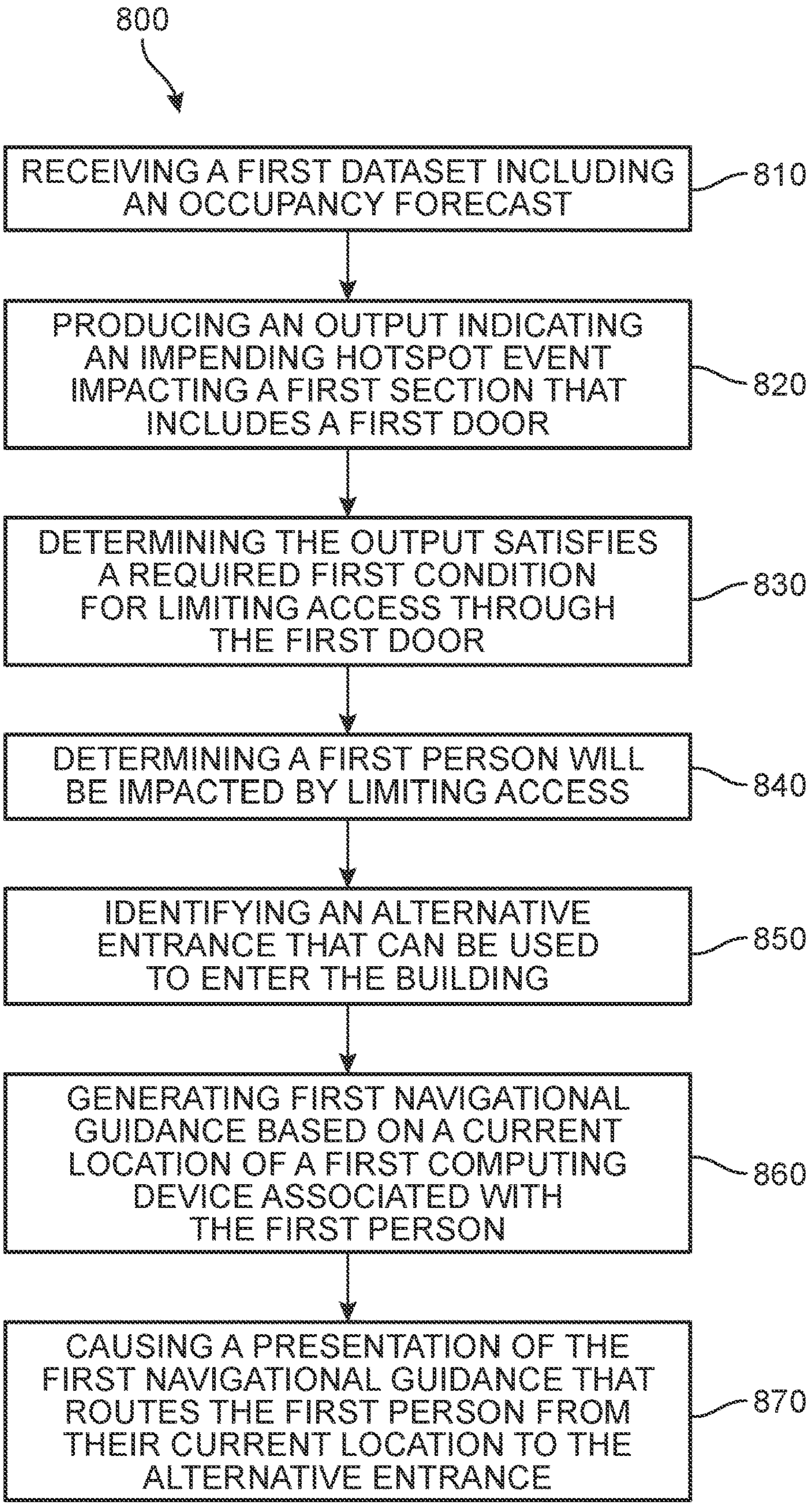
FIG. 8 is a flow chart depicting a process of providing dynamic navigational guidance in response to potential infectious conditions associated with a building, according to an embodiment.

FIG. 8 is a flow chart illustrating an embodiment of a method 800 of providing dynamic navigational guidance in response to potential infectious conditions associated with a building. The method 800 includes a first step 810 of receiving, by a contagion simulation model running on a computing device, a first dataset including an occupancy forecast, and a second step 820 of producing, via the contagion simulation model and based on the first dataset, an output indicating a high likelihood of an impending hotspot event impacting a first section of a building. For purposes of this disclosure, "impending" refers to an event that is predicted to occur within the next 7-10 days or sooner, and more commonly within the next 1-4 weeks. A third step 830 includes determining, at the computing device, the output satisfies a required first condition for limiting access through the first door, and a fourth step 840 includes determining, at an occupancy management system for the building, at least a first person will be impacted by limiting access through the first door. A fifth step 850 includes identifying, at the occupancy management system, an alternative entrance that can be used by the first person to enter the building, and a sixth step 860 includes generating first navigational guidance for the first person based on a current location of a first computing device associated with the first person. In addition, a seventh step 870 includes causing, at the first computing device, a presentation of the first navigational guidance, the navigational guidance routing the first person from their current location to a second door corresponding to the alternative entrance. For example, the presentation can occur via a mobile application, a text message, a pop-up message, a chat window, or other such electronic communication means.

In other embodiments, the method 800 may include additional steps or aspects. In some embodiments, the first hotspot event is classified under a type or category being one of an elevated disease prevalence or incidence, elevated transmission efficiency or a higher risk of disease acquisition, and increased probability of disease emergence or reemergence. In some embodiments, the first dataset is obtained from one or more sensors installed in the first section of the building. In different embodiments, the BACS can cause one or more of an automatic locking of one or more doors in the first area, an automatic spraying of cleaning agent in portions of the first area, and an automatic initiation of an ultraviolet disinfection cycle in the first area.

In some embodiments, the method 800 also includes a step of receiving, by the contagion simulation model, a set of movement rules associated with the first section. In still other embodiments, the method also includes a step of receiving, by the contagion simulation model, data regarding viral dynamics and spread for the contagion. In one example, the first condition includes a requirement that the predicted viral transmission exceed a preset threshold. In some embodiments, additional protective actions beyond limiting access to the first door are implemented in cases in which the predicted rate of transmission is above a pre-established level.

In some embodiments, the method 800 further includes steps of identifying, at the occupancy management system, a third door that can be used by the first person to enter the building, the third door being closer to the first door than the second door, receiving, at the occupancy management system, first data about a first parking lot near the second door and second data about a second parking lot near the third door, determining, at the occupancy management system, that the first parking lot has reached capacity and the second parking lot has available parking spaces, and selecting, at the occupancy management system, the second door as the alternative entrance. In another example, the method 800 can also include steps of identifying, at the occupancy management system, a third door that can be used by the first person to enter the building, the third door being closer to the first door than the second door, receiving, at the occupancy management system, first data about congestion levels near the third door, determining, at the occupancy management system, that the congestion levels exceed a first threshold, and selecting the second door as the alternative entrance. In such cases, the congestion levels for the second door can be understood to fall below the first threshold.

In one embodiment, the navigational guidance includes real-time step-by-step directions for reaching the alternative entrance (i.e., where the user's current location data—based on GPS data from the first computing device—is updated and will also cause an update to the directions being presented, on a map and/or via a set of text-based directions). In some embodiments, determining the first person will be impacted by limiting access through the first door is based on a schedule for the first person indicating they are expected to enter the first section during a time period in which the access will be limited. The schedule for various personnel associated with the building can be stored in or be otherwise electronically accessed by the occupancy management system. In another example, the determination of who will be impacted is made based on the preferences/settings selected by each of the persons, who can indicate when they should be alerted, and whether closure of a specific door should trigger a presentation of an alert to them as self-identifying as an affected/impacted person.

In different embodiments, the method 800 also includes steps of identifying, at the occupancy management system, a third door that can be used to enter the building, the third door being closer to the first door than the second door receiving, at the occupancy management system, first data about the first person indicating a mobility impairment (e.g., one that requires use of a wheelchair or the inability to climb stairs), determining, at the occupancy management system, that of the second door and third door, only the second door includes a ramp, and selecting, at the occupancy management system, the second door as the alternative entrance rather than the third door based on this fact.

Other methods can also be contemplated within the scope of this disclosure. For example, a method of providing navigational guidance in response to potential infectious conditions associated with a building is also disclosed, including a first step of receiving, by a contagion simulation model running on a computing device, a first dataset including an occupancy forecast, and a second step of producing, via the contagion simulation model and based on the first dataset, an output indicating a high likelihood of an impending hotspot event impacting a first section of the building that includes a first door. The method also includes a third step of determining, at a controller module, the output satisfies a required first condition for limiting access through the first door, and a fourth step of determining, at an occupancy management system for the building, at least a first person will be impacted by limiting access through the first door. A fifth step includes identifying, at an occupancy management system for the building, an alternative entrance that can be used to enter the building, and a sixth step includes generating first navigational guidance that describes a route from the first door to the alternative entrance. Furthermore, the method includes a seventh step of limiting access through the first door during a first time period via a building automation and control system (BACS), and an eighth step of causing a presentation of the first navigational guidance at a first computing device associated with the first person prior to or during the first time period.

In other embodiments, the method may include additional steps or aspects. In one example, the limiting of access results in disabling one or more keycards from accessing doors permitting entry to the first section. More specifically, in another example, limiting access results in a keycard associated with the first person to be disabled for use at the first door. In some embodiments, the method further includes scheduling, via the occupancy management system, of a cleaning session by a cleaning service for the first section during the first time period. In some embodiments, the method also includes causing presentation at the first computing device of a message indicating the first door has been reopened for normal access once the first time period has ended. In another example, the method includes causing the presentation of navigational guidance rerouting all personnel currently located in or near the first section to other sections of the building via their individual computing devices. Furthermore, in one embodiment, limiting access results in voiding a validity of any guest passes that were generated for visitors that had been scheduled to visit the first section via the first door.

In some other examples, the simulation model described herein is optional and the system can operate in response to real-time sensor activity. Thus, in some embodiments, the method(s) can be simplified to include a first step of receiving, by a sensor processor for a controller module, first sensor data from a first sensor installed in a first section of the building. A second step includes determining, at the controller module, the first sensor data satisfies a required criteria for implementation of a first protective response plan previously established for the building. A third step includes transmitting, from the controller module and in response to the criteria being satisfied, a control signal to a building automation and control system (BACS) for the building, the control signal causing the BACS to implement a first protective action in a first area located in the first section. Other steps described above for the previous two methods can then be employed by this streamlined process.

It is to be appreciated that methods in accordance with the present disclosure can include any combination of the aspects and features described herein. That is, methods and systems in accordance with the present disclosure are not limited to the combinations of aspects and features specifically described herein, but also include any combination of the aspects and features provided.

The processes and methods of the embodiments described in this detailed description and shown in the figures can be implemented using any kind of computing system having one or more central processing units (CPUs) and/or graphics processing units (GPUs). The processes and methods of the embodiments could also be implemented using special purpose circuitry such as an application specific integrated circuit (ASIC). The processes and methods of the embodiments may also be implemented on computing systems including read only memory (ROM) and/or random access memory (RAM), which may be connected to one or more processing units. Examples of computing systems and devices include, but are not limited to: servers, cellular phones, smart phones, tablet computers, notebook computers, e-book readers, laptop or desktop computers, all-in-one computers, as well as various kinds of digital media players.

The processes and methods of the embodiments can be stored as instructions and/or data on non-transitory computer-readable media. The non-transitory computer readable medium may include any suitable computer readable medium, such as a memory, such as RAM, ROM, flash memory, or any other type of memory known in the art. In some embodiments, the non-transitory computer readable medium may include, for example, an electronic storage device, a magnetic storage device, an optical storage device, an electromagnetic storage device, a semiconductor storage device, or any suitable combination of such devices. More specific examples of the non-transitory computer readable medium may include a portable computer diskette, a floppy disk, a hard disk, magnetic disks or tapes, a read-only memory (ROM), a random access memory (RAM), a static random access memory (SRAM), a portable compact disc read-only memory (CD-ROM), an erasable programmable read-only memory (EPROM or Flash memory), electrically erasable programmable read-only memories (EEPROM), a digital versatile disk (DVD and DVD-ROM), a memory stick, other kinds of solid state drives, and any suitable combination of these exemplary media. A non-transitory computer readable medium, as used herein, is not to be construed as being transitory signals, such as radio waves or other freely propagating electromagnetic waves, electromagnetic waves propagating through a waveguide or other transmission media (e.g., light pulses passing through a fiber-optic cable), or electrical signals transmitted through a wire.

Instructions stored on the non-transitory computer readable medium for carrying out operations of the present invention may be instruction-set-architecture (ISA) instructions, assembler instructions, machine instructions, machine dependent instructions, microcode, firmware instructions, configuration data for integrated circuitry, state-setting data, or source code or object code written in any of one or more programming languages, including an object oriented programming language such as Smalltalk, C++, or suitable language, and procedural programming languages, such as the "C" programming language or similar programming languages.

Aspects of the present disclosure are described in association with figures illustrating flowcharts and/or block diagrams of methods, apparatus (systems), and computing products. It will be understood that each block of the flowcharts and/or block diagrams can be implemented by computer readable instructions. The flowcharts and block diagrams in the figures illustrate the architecture, functionality, and operation of possible implementations of various disclosed embodiments. Accordingly, each block in the flowchart or block diagrams may represent a module, segment, or portion of instructions. In some implementations, the functions set forth in the figures and claims may occur in an alternative order than listed and/or illustrated.

The embodiments may utilize any kind of network for communication between separate computing systems. A network can comprise any combination of local area networks (LANs) and/or wide area networks (WANs), using both wired and wireless communication systems. A network may use various known communications technologies and/or protocols. Communication technologies can include, but are not limited to: Ethernet, 802.11, worldwide interoperability for microwave access (WiMAX), mobile broadband (such as CDMA, and LTE), digital subscriber line (DSL), cable internet access, satellite broadband, wireless ISP, fiber optic internet, as well as other wired and wireless technologies. Networking protocols used on a network may include transmission control protocol/Internet protocol (TCP/IP), multiprotocol label switching (MPLS), User Datagram Protocol (UDP), hypertext transport protocol (HTTP), hypertext transport protocol secure (HTTPS) and file transfer protocol (FTP) as well as other protocols.

Data exchanged over a network may be represented using technologies and/or formats including hypertext markup language (HTML), extensible markup language (XML), Atom, JavaScript Object Notation (JSON), YAML, as well as other data exchange formats. In addition, information transferred over a network can be encrypted using conventional encryption technologies such as secure sockets layer (SSL), transport layer security (TLS), and Internet Protocol security (Ipsec).

The computing devices and systems described herein may include one or more processors, a memory, one or more storage devices, and one or more input/output (1/O) devices controllable via one or more I/O interfaces. The various components may be interconnected via at least one system bus, which may enable the transfer of data between the various modules and components of the system.

The processor(s) may be configured to process instructions for execution within the system. The processor(s) may include single-threaded processor(s), multi-threaded processor(s), or both. The processor(s) may be configured to process instructions stored in the memory or on the storage device(s). The processor(s) may include hardware-based processor(s) each including one or more cores. The processor(s) may include general purpose processor(s), special purpose processor(s), or both. The memory may store information within the system. In some implementations, the memory includes one or more computer-readable media. The memory may include any number of volatile memory units, any number of non-volatile memory units, or both volatile and non-volatile memory units. The memory may include read-only memory, random access memory, or both. In some examples, the memory may be employed as active or physical memory by one or more executing software modules.

The storage device(s) may be configured to provide (e.g., persistent) mass storage for the system. In some implementations, the storage device(s) may include one or more computer-readable media. For example, the storage device(s) may include a floppy disk device, a hard disk device, an optical disk device, or a tape device. The storage device(s) may include read-only memory, random access memory, or both. The storage device(s) may include one or more of an internal hard drive, an external hard drive, or a removable drive.

One or both of the memory or the storage device(s) may include one or more computer-readable storage media (CRSM). The CRSM may include one or more of an electronic storage medium, a magnetic storage medium, an optical storage medium, a magneto-optical storage medium, a quantum storage medium, a mechanical computer storage medium, and so forth. The CRSM may provide storage of computer-readable instructions describing data structures, processes, applications, programs, other modules, or other data for the operation of the system. In some implementations, the CRSM may include a data store that provides storage of computer-readable instructions or other information in a non-transitory format. The CRSM may be incorporated into the system or may be external with respect to the system. The CRSM may include read-only memory, random access memory, or both. One or more CRSM suitable for tangibly embodying computer program instructions and data may include any type of non-volatile memory, including but not limited to: semiconductor memory devices, such as EPROM, EEPROM, and flash memory devices; magnetic disks such as internal hard disks and removable disks; magneto-optical disks; and CD-ROM and DVD-ROM disks. In some examples, the processor(s) and the memory may be supplemented by, or incorporated into, one or more application-specific integrated circuits (ASICs).

The system may include one or more I/O devices. The I/O device(s) may include one or more input devices such as a keyboard, a mouse, a pen, a game controller, a touch input device, an audio input device (e.g., a microphone), a gestural input device, a haptic input device, an image or video capture device (e.g., a camera), or other devices. In some examples, the I/O device(s) may also include one or more output devices such as a display, LED(s), an audio output device (e.g., a speaker), a printer, a haptic output device, and so forth. The I/O device(s) may be physically incorporated in one or more computing devices of the system, or may be external with respect to one or more computing devices of the system.

The system may include one or more I/O interfaces to enable components or modules of the system to control, interface with, or otherwise communicate with the I/O device(s). The I/O interface(s) may enable information to be transferred in or out of the system, or between components of the system, through serial communication, parallel communication, or other types of communication. For example, the I/O interface(s) may comply with a version of the RS-232 standard for serial ports, or with a version of the IEEE 1284 standard for parallel ports. As another example, the I/O interface(s) may be configured to provide a connection over Universal Serial Bus (USB) or Ethernet. In some examples, the I/O interface(s) may be configured to provide a serial connection that is compliant with a version of the IEEE 1394 standard. The I/O interface(s) may also include one or more network interfaces that enable communications between computing devices in the system, or between the system and other network-connected computing systems. The network interface(s) may include one or more network interface controllers (NICs) or other types of transceiver devices configured to send and receive communications over one or more networks, such as the network(s), using any network protocol.

Computing devices of the system may communicate with one another, or with other computing devices, using one or more networks. Such networks may include public networks such as the internet, private networks such as an institutional or personal intranet, or any combination of private and public networks. The networks may include any type of wired or wireless network, including but not limited to local area networks (LANs), wide area networks (WANs), wireless WANs (WWANs), wireless LANs (WLANs), mobile communications networks (e.g., 3G, 4G, Edge, etc.), and so forth. In some implementations, the communications between computing devices may be encrypted or otherwise secured. For example, communications may employ one or more public or private cryptographic keys, ciphers, digital certificates, or other credentials supported by a security protocol, such as any version of the Secure Sockets Layer (SSL) or the Transport Layer Security (TLS) protocol.

The system may include any number of computing devices of any type. The computing device(s) may include, but are not limited to: a personal computer, a smartphone, a tablet computer, a wearable computer, an implanted computer, a mobile gaming device, an electronic book reader, an automotive computer, a desktop computer, a laptop computer, a notebook computer, a game console, a home entertainment device, a network computer, a server computer, a mainframe computer, a distributed computing device (e.g., a cloud computing device), a microcomputer, a system on a chip (SoC), a system in a package (SiP), and so forth. Although examples herein may describe computing device (s) as physical device(s), implementations are not so limited. In some examples, a computing device may include one or more of a virtual computing environment, a hypervisor, an emulation, or a virtual machine executing on one or more physical computing devices. In some examples, two or more computing devices may include a cluster, cloud, farm, or other grouping of multiple devices that coordinate operations to provide load balancing, failover support, parallel processing capabilities, shared storage resources, shared networking capabilities, or other aspects.

Implementations and all of the functional operations described in this specification may be realized in digital electronic circuitry, or in computer software, firmware, or hardware, including the structures disclosed in this specification and their structural equivalents, or in combinations of one or more of them. Implementations may be realized as one or more computer program products, i.e., one or more modules of computer program instructions encoded on a computer readable medium for execution by, or to control the operation of, data processing apparatus. The computer readable medium may be a machine-readable storage device, a machine-readable storage substrate, a memory device, a composition of matter effecting a machine-readable propagated signal, or a combination of one or more of them. The term "computing system" encompasses all apparatus, devices, and machines for processing data, including by way of example a programmable processor, a computer, or multiple processors or computers. The apparatus may include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

A computer program (also known as a program, software, software application, script, or code) may be written in any appropriate form of programming language, including compiled or interpreted languages, and it may be deployed in any appropriate form, including as a standalone program or as a module, component, subroutine, or other unit suitable for use in a computing environment. A computer program does not necessarily correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may be deployed to be executed on one computer or on multiple computers that are located at one site or distributed across multiple sites and interconnected by a communication network.

The processes and logic flows described in this specification may be performed by one or more programmable processors executing one or more computer programs to perform functions by operating on input data and generating output. The processes and logic flows may also be performed by, and apparatus may also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any appropriate kind of digital computer. Generally, a processor may receive instructions and data from a read only memory or a random access memory or both. Elements of a computer can include a processor for performing instructions and one or more memory devices for storing instructions and data. Generally, a computer may also include, or be operatively coupled to receive data from or transfer data to, or both, one or more mass storage devices for storing data, e.g., magnetic, magneto optical disks, or optical disks. However, a computer need not have such devices. Moreover, a computer may be embedded in another device, e.g., a mobile telephone, a personal digital assistant (PDA), a mobile audio player, a GPS receiver, to name just a few. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory may be supplemented by, or incorporated in, special purpose logic circuitry.

To provide for interaction with a user, implementations may be realized on a computer having a display device, e.g., a CRT (cathode ray tube) or LCD (liquid crystal display) monitor, for displaying information to the user and a keyboard and a pointing device, e.g., a mouse or a trackball, by which the user may provide input to the computer. Other kinds of devices may be used to provide for interaction with a user as well; for example, feedback provided to the user may be any appropriate form of sensory feedback, e.g., visual feedback, auditory feedback, or tactile feedback; and input from the user may be received in any appropriate form, including acoustic, speech, or tactile input.

Implementations may be realized in a computing system that includes a back end component, e.g., as a data server, or that includes a middleware component, e.g., an application server, or that includes a front end component, e.g., a client computer having a graphical user interface or a web browser through which a user may interact with an implementation, or any appropriate combination of one or more such back end, middleware, or front end components. The components of the system may be interconnected by any appropriate form or medium of digital data communication, e.g., a communication network. Examples of communication networks include a local area network ("LAN") and a wide area network ("WAN"), e.g., the Internet. The computing system may include clients and servers. A client and server are generally remote from each other and typically interact through a communication network. The relationship of client and server arises by virtue of computer programs running on the respective computers and having a client-server relationship to each other.

While this specification contains many specifics, these should not be construed as limitations on the scope of the disclosure or of what may be claimed, but rather as descriptions of features specific to particular implementations. Certain features that are described in this specification in the context of separate implementations may also be implemented in combination in a single implementation. Conversely, various features that are described in the context of a single implementation may also be implemented in multiple implementations separately or in any suitable sub-combination. Moreover, although features may be described above as acting in certain combinations and even initially claimed as such, one or more features from a claimed combination may in some examples be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems may generally be integrated together in a single software product or packaged into multiple software products.

While various embodiments of the invention have been described, the description is intended to be exemplary, rather than limiting, and it will be apparent to those of ordinary skill in the art that many more embodiments and implementations are possible that are within the scope of the invention. Accordingly, the invention is not to be restricted except in light of the attached claims and their equivalents. Also, various modifications and changes may be made within the scope of the attached claims.

We claim:

1. A non-transitory computer-implemented method of providing dynamic navigational guidance in response to infectious conditions associated with a building, the method comprising:

downloading a mobile app on a mobile computing device associated with a first person;

receiving, by a contagion simulation model running on a sensor data processor, a first dataset including an occupancy forecast;

producing, via the contagion simulation model and based on the first dataset, an output indicating an impending hotspot event impacting a first section of the building that includes a first door;

providing the first person with a keycard for use at the first door;

determining, at a controller module, the output satisfies a required first condition for limiting access through the first door;

limiting access through the first door by disabling the key card;

determining, at an occupancy management system for the building, at least the first person will be impacted by limiting access through the first door;

identifying, at the occupancy management system, an alternative entrance to the building;

generating first navigational guidance for the first person based on a current location of said mobile computing device; and causing, on said mobile computing device, a presentation of the first navigational guidance, the navigational guidance routing the first person from their current location to a second door corresponding to the alternative entrance, the navigational guidance including real-time step-by-step instructions for reaching the alternative entrance.

2. The method of claim 1, wherein the first hotspot event is classified as one of an elevated disease prevalence or incidence, elevated transmission efficiency or a higher risk of disease acquisition, and increased probability of disease emergence or reemergence.

3. The method of claim 1, wherein the first dataset is obtained from one or more sensors installed in the first section of the building.

4. The method of claim 1, further comprising:

identifying, at the occupancy management system, a third door to the building, the third door being closer to the first door than the second door;

receiving, at the occupancy management system, first data about a first parking lot near the second door and second data about a second parking lot near the third door;

determining, at the occupancy management system, that the first parking lot has reached capacity and the second parking lot has available parking spaces; and selecting, at the occupancy management system, the third door as the alternative entrance.

5. The method of claim 1, further comprising:

identifying, at the occupancy management system, a third door to the building, the third door being closer to the first door than the second door;

receiving, at the occupancy management system, first data about congestion levels near the third door;

determining, at the occupancy management system, that the congestion levels exceed a first threshold; and selecting the second door as the alternative entrance.

6. The method of claim 1, wherein determining the first person will be impacted by limiting access through the first door is based on a schedule for the first person indicating the first person is expected to enter the first section during a time period in which the access will be limited.

7. The method of claim 1, further comprising:

identifying, at the occupancy management system, a third door to the building, the third door being closer to the first door than the second door;

receiving, at the occupancy management system, first data about the first person indicating a mobility impairment;

determining, at the occupancy management system, that only the second door includes a ramp; and selecting, at the occupancy management system, the second door as the alternative entrance rather than the third door.

8. The method of claim 1, further comprising receiving, by the contagion simulation model, data regarding viral dynamics and spread for the contagion.

9. The method of claim 1, wherein the first condition includes a requirement that the predicted viral transmission exceed a preset threshold.

10. The method of claim 1, further comprising reenabling the key card once the output no longer satisfies the required first condition for limiting access through the first door.

11. The method of claim 1 further comprising presentation at the mobile computing device of a message indicating the first door has been reopened for normal access once the output no longer satisfies the required first condition for limiting access through the first door.

12. A non-transitory computer-implemented method of providing navigational guidance in response to infectious conditions associated with a building, the method comprising:

downloading a mobile app on a mobile computing device associated with a first person;

receiving, by a contagion simulation model running on a sensor data processor, a first dataset including an occupancy forecast;

producing, via the contagion simulation model and based on the first dataset, an output indicating an impending hotspot event impacting a first section of the building that includes a first door;

providing the first person with a keycard for use at the first door;

determining, at a controller module, the output satisfies a required first condition for limiting access through the first door;

determining, at an occupancy management system for the building, at least the first person will be impacted by limiting access through the first door;

identifying, at an occupancy management system for the building, an alternative entrance to the building;

generating first navigational guidance that describes a route from the first door to the alternative entrance;

limiting access through the first door during a first time period via a building automation and control system (BACS) disabling the key card; and causing, on said mobile computing device a presentation of the first navigational guidance prior to or during the first time period, the navigational guidance including real-time step-by-step instructions for reaching the alternative entrance from the first door.

13. The method of claim 12, further comprising scheduling, via the occupancy management system, a cleaning session by a cleaning service for the first section during the first time period.

14. The method of claim 12, further comprising causing presentation at the mobile computing device of a message indicating the first door has been reopened for normal access once the first time period has ended.

15. A system for providing dynamic navigational guidance in response to potential infectious conditions associated with a building, the system comprising a processor, a mobile computing device associated with a first person, a keycard provided to a first person for use at a first door of the building, and machine-readable media including instructions which, when executed by the processor, cause the processor to:

download a mobile app on the mobile computing device;

receive, by a contagion simulation model running on a sensor data processor, a first dataset including an occupancy forecast;

produce, via the contagion simulation model and based on the first dataset, an output indicating an impending hotspot event impacting a first section of the building that includes the first door;

determine, at a controller module, the output satisfies a required first condition for limiting access through the first door;

limit access through the first door by disabling the key card;

determine, at an occupancy management system for the building, at least the first person will be impacted by limiting access through the first door;

identify, at the occupancy management system, an alternative entrance to the building;

generate first navigational guidance for the first person based on a current location of the mobile computing device; and cause, at the mobile computing device, a presentation of the first navigational guidance, the navigational guidance routing the first person from their current location to a second door corresponding to the alternative entrance, the navigational guidance including real-time step-by-step instructions for reaching the second door.

16. The system of claim 15, wherein the first dataset is obtained from one or more sensors installed in the first section of the building.

17. The system of claim 15, wherein the instructions further cause the processor to:

identify, at the occupancy management system, a third door to the building, the third door being closer to the first door than the second door;

receive, at the occupancy management system, first data about a first parking lot near the second door and second data about a second parking lot near the third door;

determine, at the occupancy management system, that the first parking lot has reached capacity and the second parking lot has available parking spaces; and select, at the occupancy management system, the third door instead of the second door as the alternative entrance.

18. The system of claim 15, wherein the instructions further cause the processor to:

identify, at the occupancy management system, a third door to the building, the third door being closer to the first door than the second door;

receive, at the occupancy management system, first data about congestion levels near the third door;

determine, at the occupancy management system, that the congestion levels exceed a first threshold; and select the second door as the alternative entrance.

19. The system of claim 15, wherein determining the first person will be impacted by limiting access through the first door is based on a schedule for the first person indicating they are expected to enter the first section during a time period in which the access will be limited.

20. The system of claim 15, wherein the instructions further cause the processor to:

identify, at the occupancy management system, a third door to the building, the third door being closer to the first door than the second door;

receive, at the occupancy management system, first data about the first person indicating a mobility impairment;

determine, at the occupancy management system, that only the second door includes a ramp; and select, at the occupancy management system, the second door as the alternative entrance rather than the third door.

* * * * *